(12) United States Patent
Choi et al.

(10) Patent No.: US 7,078,537 B2
(45) Date of Patent: Jul. 18, 2006

(54) PHENYLALKYL DIAMINE AND AMIDE ANALOGS

(75) Inventors: Yong-Moon Choi, Towaco, NJ (US); Yong-Kil Kim, Taejon (KR); Chun-Eung Park, Taejon (KR); Eun-Ho Lee, Taejon (KR)

(73) Assignee: SK Corporation (KR)

( * ) Notice: Subject to any disclaimer, the term of this patent is extended or adjusted under 35 U.S.C. 154(b) by 228 days.

(21) Appl. No.: 10/170,076

(22) Filed: Jun. 12, 2002

(65) Prior Publication Data

US 2003/0105079 A1    Jun. 5, 2003

Related U.S. Application Data

(60) Provisional application No. 60/297,504, filed on Jun. 12, 2001.

(51) Int. Cl.
*C07D 207/08*    (2006.01)
*C07D 207/10*    (2006.01)
*C07D 207/46*    (2006.01)

(52) U.S. Cl. ............. 548/566; 544/402; 544/162; 540/609; 546/229

(58) Field of Classification Search ........... 548/566; 544/402, 162; 540/609; 546/229; 514/217.12, 514/237.8, 252.12, 317, 408
See application file for complete search history.

(56) References Cited

U.S. PATENT DOCUMENTS

| | | | | |
|---|---|---|---|---|
| 2,742,460 | A | * | 4/1956 | Murphy et al. ............ 540/341 |
| 2,798,072 | A | * | 7/1957 | Pohland ................... 546/234 |
| 2,850,498 | A | * | 9/1958 | Pohland ................... 546/234 |
| 4,764,617 | A | * | 8/1988 | Masaki et al. ............ 546/169 |
| 5,030,649 | A | * | 7/1991 | Vecchietti et al. ........ 436/64 |
| 5,134,238 | A | * | 7/1992 | Rossiter et al. ........... 546/11 |
| 5,646,151 | A | | 7/1997 | Kruse et al. |
| 5,804,595 | A | * | 9/1998 | Portoghese et al. ....... 514/428 |

FOREIGN PATENT DOCUMENTS

| EP | 256181 | * | 2/1988 |
|---|---|---|---|
| WO | WO 97/46553 | * | 12/1997 |

OTHER PUBLICATIONS

Cignarella et al., Syntheses and κ binding affinity of 1-(pyrrolidin-1-methyl)-2-(N-methyl)-4-[(3,4-dichloro)phenyl]-1,2,3,4-tetrahydroisoquinolin-3(2H)-ones, Eur. J. Med Chem. (1995), 515-520.*

Kumar et al., Arylacetamides as Peripherally Restricted Kappa Opioid Receptor Agonists, Bioorganic & Medical Chemistry Letters 10 (2000) 2567-2570.*

Singh et al., An Effective Synthesis of Chiral Nonracemic Diamines: Application in Asymmetric Synthesis, Tetrahedron Letters, 39, 1998, 167-170.*

O'Brien et al., Practical One-Step Synthesis of Koga's Chiral Bases, Synthesis, 2001, 5, 693-695.*

Borisova et al., Aminoamides. III. I-Dialkylamino-3-phenyl-3-acylaminopropanes and I-Dialkylamino-3-phenyl-3-acylaminopropanes, Zhurnal Organicheskoi Khimii, 1969, 5 (2), 284-286.*

Moehrle et al., Syntheses of Amino Lactams and Amidines, Archiv der Pharmazie (Weinheim, Germany) 1973, 306 (5), 325-338.*

Moehrle et al., Neighboring Group Effects of Aliphatic Amines, Archiv der Pharmazie (Weinheim, Germany) 1973, 306 (3), 209-226.*

Curthbertson, Eric, et al., Practical One-Step Synthesis of Koga's Chiral Bases, Dec. 4, 2001, pp. 693-695, Synthesis 2001, No. 5.

* cited by examiner

*Primary Examiner*—Johann Richter
*Assistant Examiner*—Chukwuma Nwaonicha
(74) *Attorney, Agent, or Firm*—Gibbons, Del Deo, Dolan, Griffinger, and Vecchione

(57) ABSTRACT

The present invention relates to novel 1,2- or 1,3-diamine and amide compounds and pharmaceutically useful salts thereof and methods for treating central nervous system diseases. The present 1,2- or 1,3-diamine and amide compounds have high binding affinity to the sigma receptor.

15 Claims, No Drawings

PHENYLALKYL DIAMINE AND AMIDE ANALOGS

REFERENCE TO RELATED APPLICATION

This Application claims priority from U.S. Provisional Application 60/297,504 filed Jun. 12, 2001.

FIELD OF THE INVENTION

The present invention relates, in general, to novel 1,2- or 1,3-diamine and amide compounds and pharmaceutically useful salts thereof and methods for treating central nervous system diseases. More particularly, the present invention relates to 1,2- or 1,3-diamine and amide compounds having high binding affinity to the sigma receptor and pharmaceutical compositions thereof.

BACKGROUND OF THE INVENTION

Phenylalkylamine derivatives, one important class of therapeutic medicines that is useful in managing central nervous system (CNS) diseases, have been used mainly to treat obesity, narcolepsy, minimal brain dysfunction and mild depression.

Diamine or amide compounds have been effectively used for controlling various CNS disorders. For example, International Patent Application No. WO 93/22279 discloses 1,2-diamine derivatives that are psychotropic agents particularly suitable for treating psychotic disorders, convulsion, dyskinesia, brain distress and anxiety. Further, N-(arylethyl)-N-alkyl-2-(1-pyrrolidinyl)ethylamine has been demonstrated to bind the sigma receptor. J. Med. Chem. 35, 38 (1992)

The physical and pharmaceutical nature of the sigma receptor has not been fully defined. However, evidence indicates that sigma receptors have a number of biological functions, including motor effects, regulation of dopamine and acetylcholine release, modulation of the NMDA-evoked norepinephrine release, antagonism of opioid analgesia, and mediation of the functional activity of the immune cells. Potential applications of sigma ligands are the treatment of psychosis, dystonia, motor dysfunctions, ischemia, anxiety, epilepsy, convulsion and senile dementia, etc. For example, International Patent Publication No. WO9014067 discloses some guanidine derivatives having sigma receptor activity which are useful as anxielytics.

Accordingly, agents potently acting on the sigma receptors may be useful in the therapy of these conditions. Also, creating the specific drug for sigma receptor interaction and finding the novel pharmacological effect are important for developing new type of drugs.

SUMMARY OF THE INVENTION

As a result of intensive and thorough research, it has been found that phenylalkyl diamine and amide compounds strongly bind to the sigma receptors.

Accordingly, a principal object of the present invention is to provide racemic phenylalkyl diamine or amide compounds represented by the following general Formula I and their pharmaceutically acceptable salts.

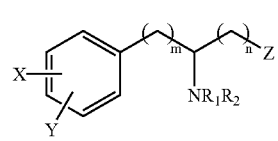

wherein
m is 0–2;
n is 1–4;
X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy, or trifluoromethyl;
$R_1$ and $R_2$ are independently hydrogen, lower alkyl, benzyl, substituted benzyl, phenylalkyl, substituted phenylalkyl, benzoyl, substituted benzoyl, formyl, acetyl, phenyl acetyl, substituted phenyl acetyl, methansulfonyl, benzenesulfonyl, or substituted benzenesulfonyl; and
Z is 5 to 7-membered aliphatic cyclic amine compounds including pyrrolidine, piperidine, hexamethyleneimine, morpholine, 4-benzylpiperidine, N-benzylpiperazine, or substituted 4-benzoylpiperidine derivatives having the general formula (II) or (II')

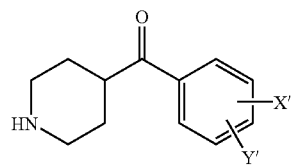

wherein
X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, or trifluoromethyl.

It is also a principal object of the present invention to provide d-phenylalkyl diamine or amide compounds represented by the following general formula III and their pharmaceutically acceptable salts. (alternatively, 'd' can be referred to as the R-configuration at the chiral center in structural formula III)

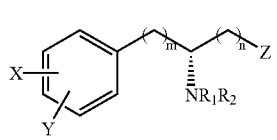

wherein
m is 0–2;
n is 1–4;

X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy, or trifluoromethyl;

$R_1$ and $R_2$ are independently hydrogen, lower alkyl, benzyl, substituted benzyl, phenylalkyl, substituted phenylalkyl, benzoyl, substituted benzoyl, formyl, acetyl, phenyl acetyl, substituted phenyl acetyl, methansulfonyl, benzenesulfonyl, substituted benzenesulfonyl; and Z is 5 to 7-membered aliphatic cyclic amine compounds including pyrrolidine, piperidine, hexamethyleneimine, morpholine, 4-benzylpiperidine, N-benzylpiperazine, substituted 4-benzoylpiperidine having the general formula (II) or (II').

Another object of the present invention to provide 1-phenylalkyl diamine or amide compounds represented by the following general formula IV and their pharmaceutically acceptable salts. (alternatively, 'l' can be referred to as the S-configuration at the chiral center in structural formula IV)

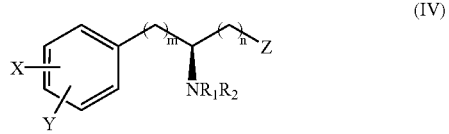

(IV)

wherein
m is 0–2;
n is 1–4;

X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy, or trifluoromethyl;

$R_1$ and $R_2$ are independently hydrogen, lower alkyl, benzyl, substituted benzyl, phenylalkyl, substituted phenylalkyl, benzoyl, substituted benzoyl, formyl, acetyl, phenyl acetyl, substituted phenyl acetyl, methansulfonyl, benzenesulfonyl, substituted benzenesulfonyl; and Z is 5 to 7-membered aliphatic cyclic amine compounds including pyrrolidine, piperidine, hexamethyleneimine, morpholine, 4-benzylpiperidine, N-benzylpiperazine, substituted 4-benzoylpiperidine having the general formula (II) or (II').

DETAILED DESCRIPTION OF THE INVENTION

In accordance with the present invention, the compounds of this invention represented by the structural formula I, III, IV and pharmaceutically acceptable salts thereof can be prepared by the following steps starting from readily available starting materials represented by the following general formula (V)

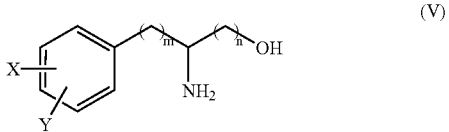

(V)

wherein X, Y, m and n are the same as defined above.

It should be noted that the stereochemistry of the final products (I, III and IV) depend solely on that of the starting material (V); a starting material (V) with an d-enantiomer yields only a product with d-enantiomer (III) and a starting material (V) with an l-enantiomer yields only a product with l-enantiomer (IV).

The method for preparing the novel compounds of the general formula I in which $R_1$ and $R_2$ are hydrogen will be described below in detail.

Initially, aminoalkanol (V) is reacted with di-t-butyl dicarbonate to synthesize N-t-butyloxycarbonyl-aminoalkanol represented by the general formula (VI).

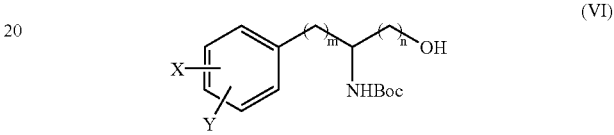

(VI)

The compound of formula VI is treated with triphenylphosphine and N-bromosuccinimide in dimethylformamide solution to yield the corresponding bromide compound represented by the general formula (VII).

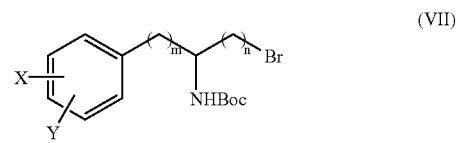

(VII)

The compound of formula VII is treated with an amine base Z to yield N-Boc-diamine compounds represented by the general formula (VIII)

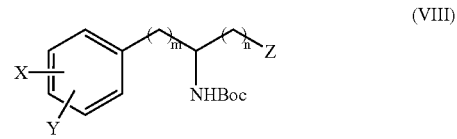

(VIII)

wherein X, Y, m, n and Z are as defined above and Boc represents t-butyloxy carbonyl radical. Next, this intermediate is deprotected by methanolic hydrochloric acid solution resulting in diamine compounds represented by the general formula (IX). The compound of formula (IX) may be converted into pharmaceutically acceptable salts (X) as described above.

This procedure is summarized as set forth in Scheme 1 below.

Scheme 1

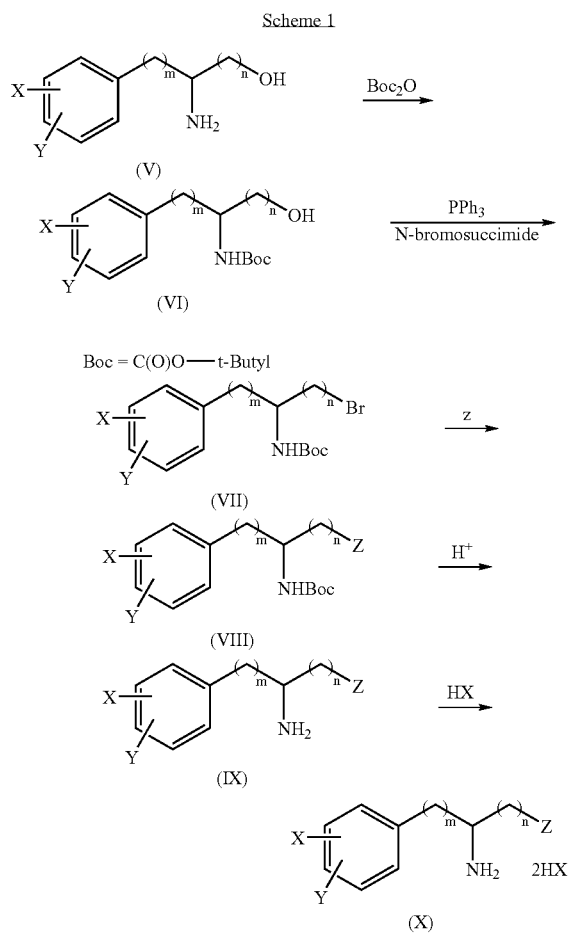

Reaction Conditions of Scheme 1

In the first step, the concentration of the starting material (V) is about 0.005 to 3 moles with di-t-butyl dicarbonate ranging from about 1.0 to 2.0 equivalents. The basic aqueous solution has a pH value between about 7 and 14 and the conversion is carried out at temperature from about −10 to 70°. Compound (VI) is converted to compound (VII) using triphenylphosphine and N-bromosuccinimide ranging from about 1.0 to 2.5 equivalent, preferably carried out at a temperature of about 20 to 50° in dimethylformamide. The compound of the general formula (VIII) is formed by treating compound (VII) with 1 to 5 equivalents of amine, Z, at a temperature of about 30 to 120°. For this conversion, an ethereal solvent, such as tetrahydrofuran and dioxane, or a polar aprotic solvent, such as dimethylformamide and dimethyl sulfoxide, or aromatic hydrocarbons such as benzene, toluene and xylene, or lower aliphatic alcohols, such as methanol, ethanol, isopropanol, is employed. Compound (VIII) is treated with methanolic 6% hydrochloric acid at a temperature of about −10 to 30°, followed by neutralization to yield the compound of the general formula (IX).

In the scheme 1, HX represents an acid capable of forming a pharmacologically useful salt with the basic nitrogen atom. Specific examples of the anhydrous acid used for the preparation of the compound (X) from the compound is (IX) include but not limited to: hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. This preparation is executed in a reaction media which can be exemplified by an ethereal solvent such as THF, an alcoholic solvent such as methanol, an ester solvent such as ethyl acetate, and aromatic solvent, and any compositional mixture thereof. An ethereal solvent is recommended as an addition solution, including ethyl ether, propyl ether, isopropyl ether, butyl ether, isobutyl ether. The concentration of the compound (IX) is on the order of about 0.01 to 5 mole.

The method for preparing the novel compounds of the general formula I in which $R_1$ and/or $R_2$ are not hydrogen is described below.

Initially, the prepared diamine compounds (IX), in which $R_1=R_2=H$, is reacted with triethylamine and an appropriate acyl chloride in dichloromethane at 0° or ethyl formate at reflux condition to yield the amide compounds represented by the general formula (XI)

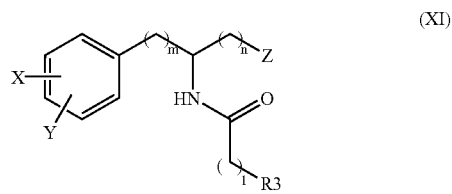

wherein X, Y, m, n and Z are as defined above, l is 0–3, and R3 are same or different and hydrogen or substituted aromatic ring such as phenyl or 3,4-dichlorophenyl.

The compound (XI) is treated with 1M Alane or LiAlH$_4$ in THF to yield the N-alkylated compounds represented by the general formula (XII)

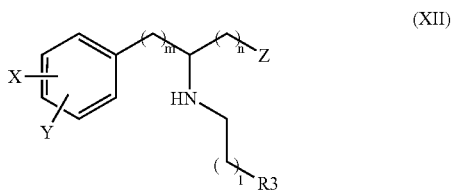

wherein X, Y, l, m, n, Z and R3 are as defined above.

Using the same method and compound (XII) as the starting compound, the compound (XVI) and (XVII) are obtained.

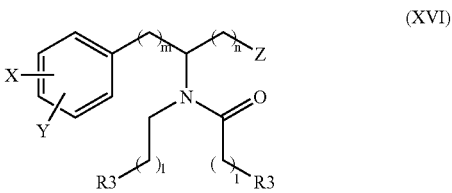

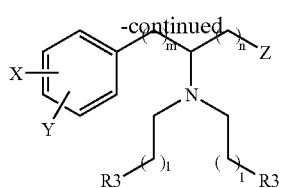

wherein X, Y, 1, m, n, Z and R3 are as defined above.

Compounds of formula (XI), (XII), (XVI), (XVII) may be converted into pharmaceutically acceptable salts (XIII) as described above.

This procedure is summarized as set forth in Scheme 2 below.

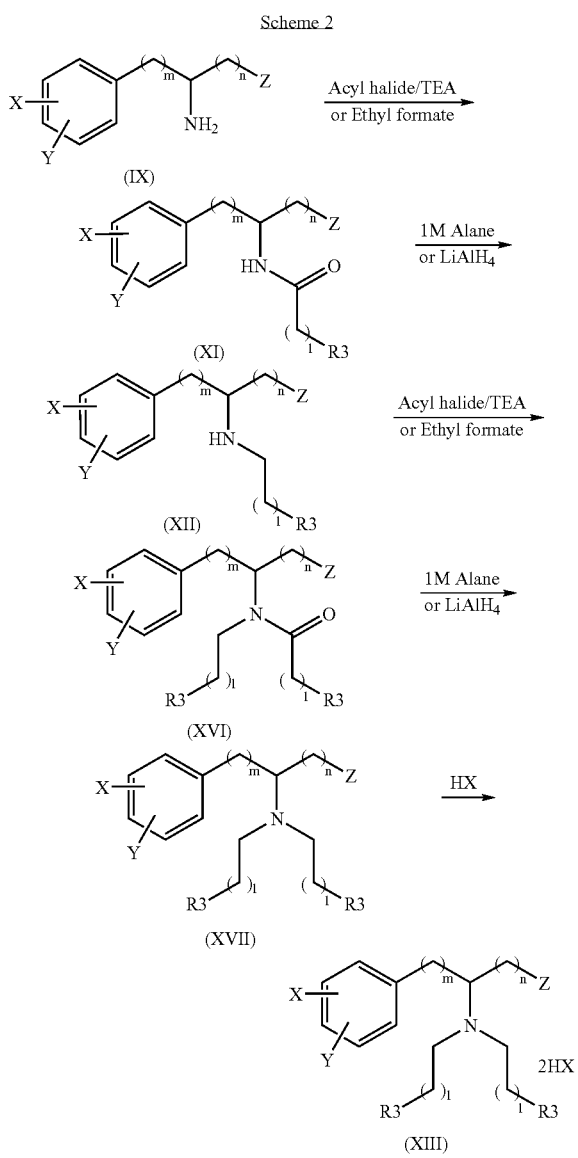

Reaction Conditions of Scheme 2

In the first step, compound (IX) to the compound (XI) is converted to compound (IX) using triethylamine and acyl halide ranging from about 1.0 to 1.5 equivalents preferably at a temperature of about −10 to 20° in dichloromethane. In another method, compound (IX) is converted to compound (XI) is by refluxing compound (IX) with ethyl formate as reagent and solvent. The compound of general formula (XII) is formed by is reducing compound (XI) with 1 to 5 equivalents of 1M Alane or LiAlH$_4$ in THF at a room temperature. Using the same methods as described for the conversion of compound (IX) to the compounds (XI) and (XII), compounds (XVI) and (XVII) are obtained from compound (XII). In Scheme 2, HX represents an acid capable of forming a pharmacologically useful salt with the basic nitrogen atom.

Another method for preparing the novel compounds of the general formula I in which R$_1$ and/or R$_2$ are not Hydrogen is described below.

Initially, the prepared diamine compounds (IX), in which R$_1$=R$_2$=H, is reacted with triethylamine and an appropriate sulfonyl chloride in dichloromethane at 0° to yield the sulfonamide compounds represented by the general formula (XIV)

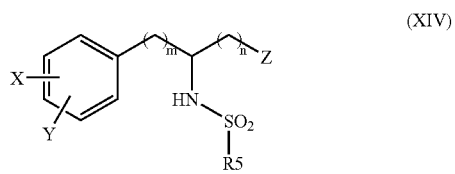

wherein X, Y, m, n and Z are as defined above and R5 are methyl or substituted aromatic ring such as phenyl, 2-nitrophenyl, 4-methylphenyl, 2,4-dinitrophenyl, 3-nitrophenyl, 2,4,6-triisopropylphenyl, 2-thiophenyl. The compound of formula (XIV) may be converted into pharmaceutically acceptable salts (XV) as described above. This procedure is summarized as set forth in Scheme 3 below.

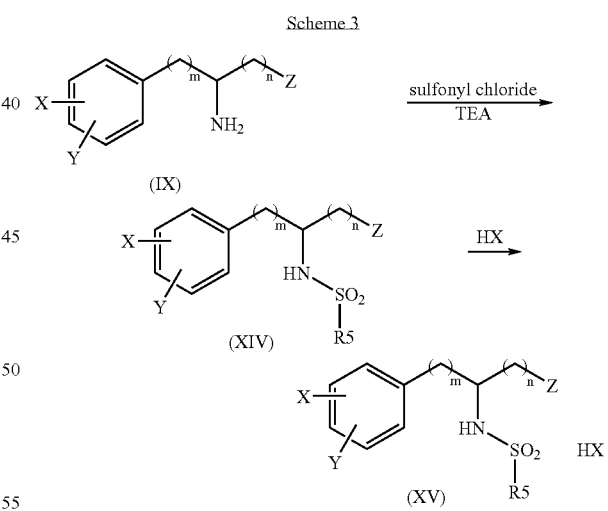

Reaction Conditions of Scheme 3

Compound (IX) is converted to the compound (XIV), using triethylamine and sulfonyl chloride ranging from about 1.0 to 1.5 equivalents, preferably carried out at a temperature of about −10 to 20° in dichloromethane.

In Scheme 3, HX represents an acid capable of forming a pharmacologically useful salt with the basic nitrogen atom.

Representative examples of the compounds (I), (III) and (IV) from scheme 1, 2 and 3 include the following structures:

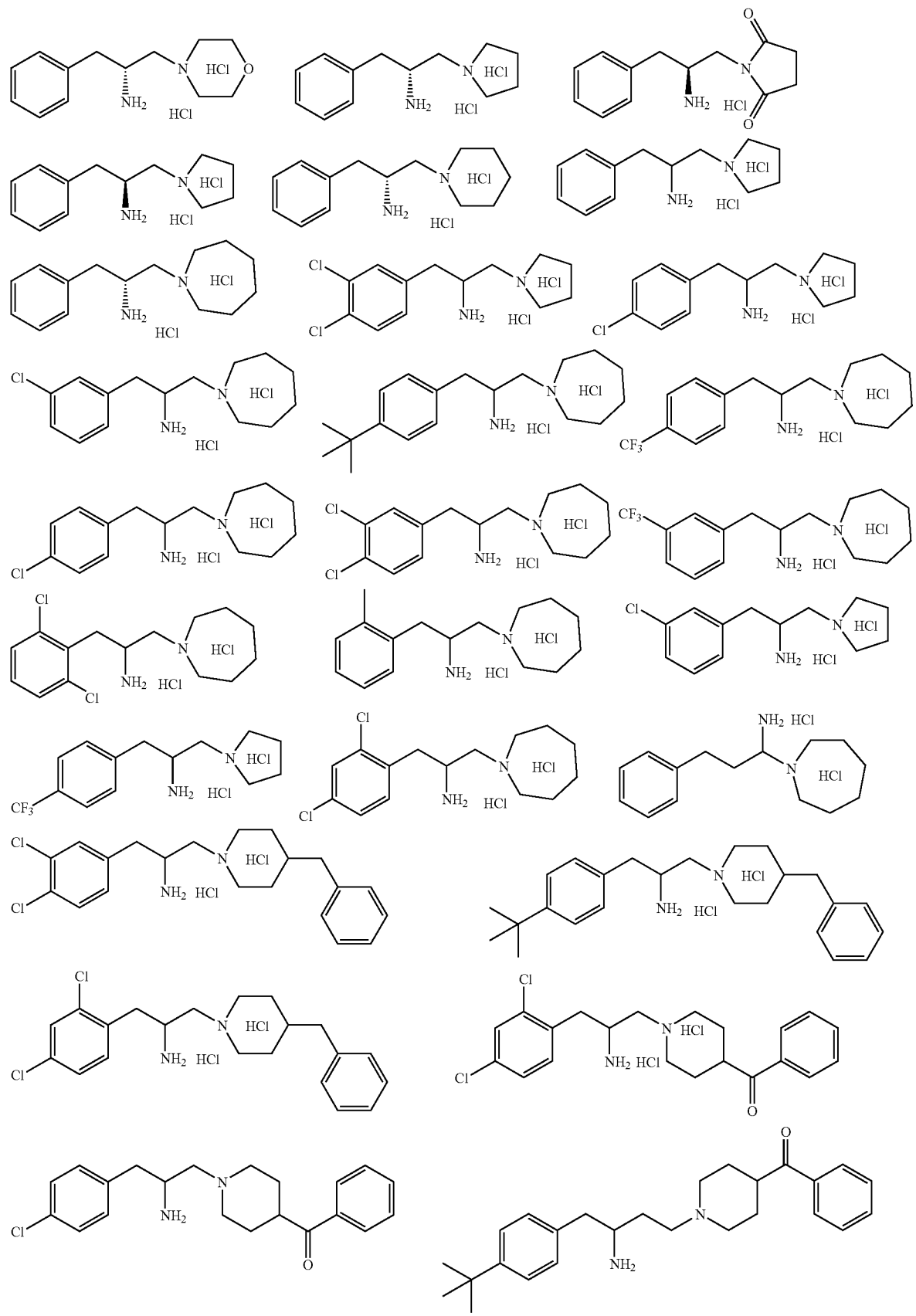

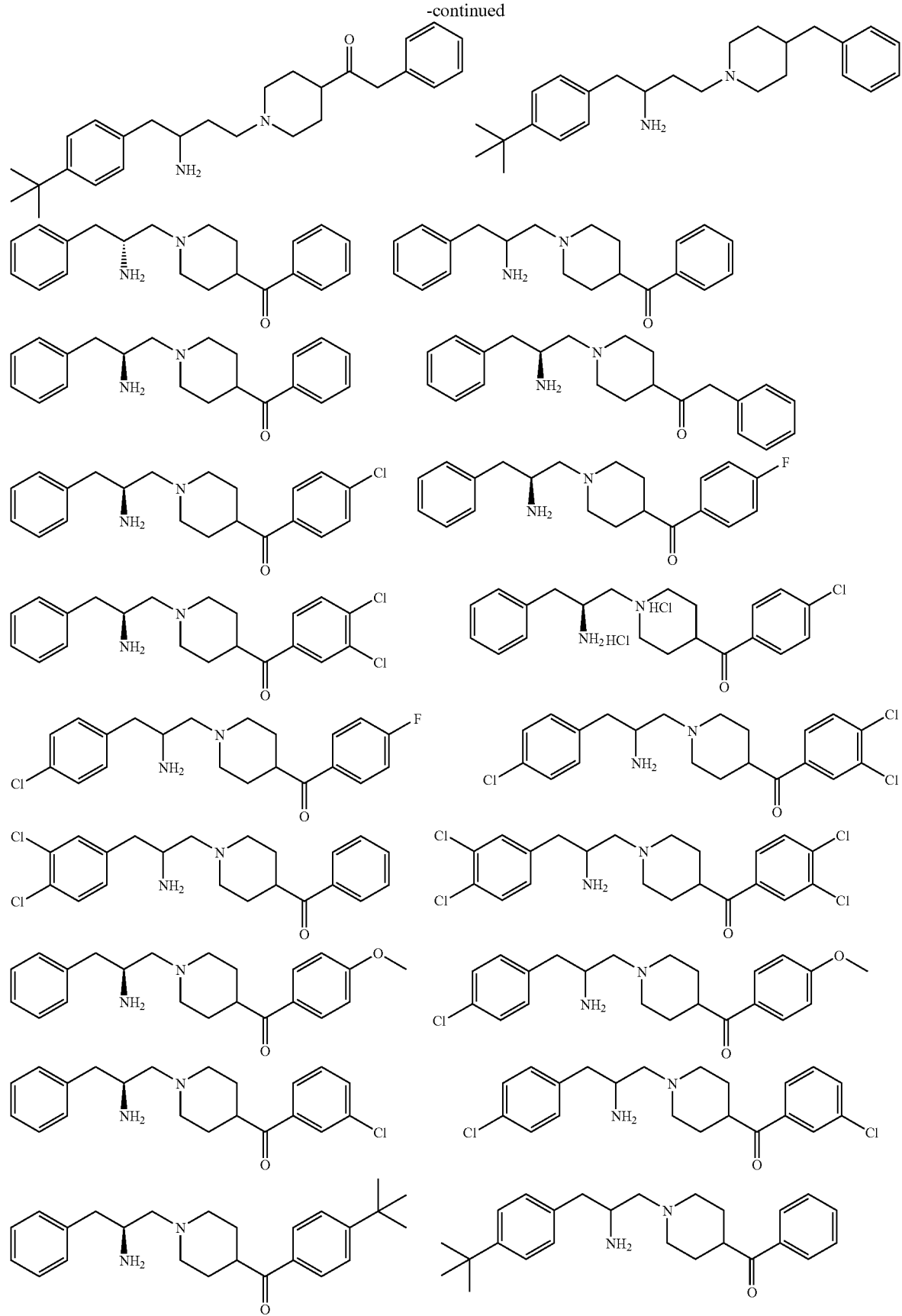

-continued
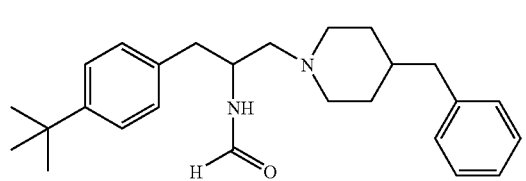
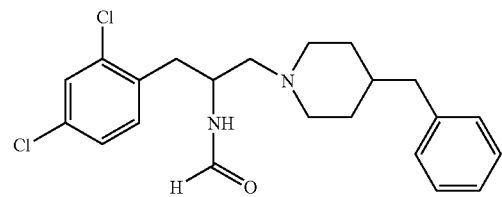
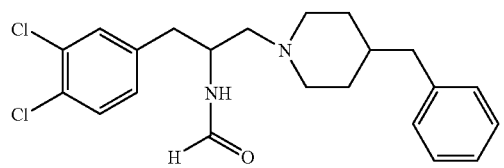
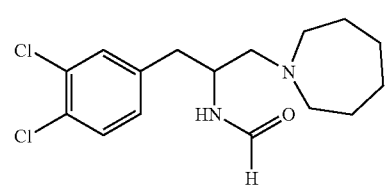
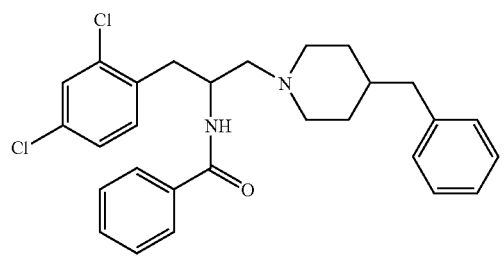
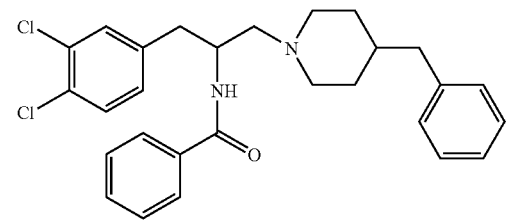
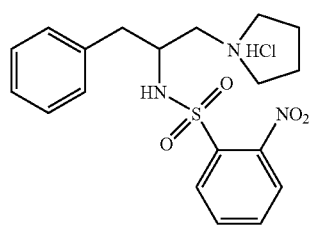
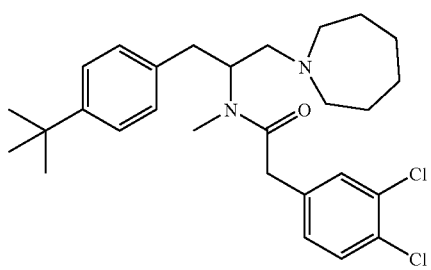
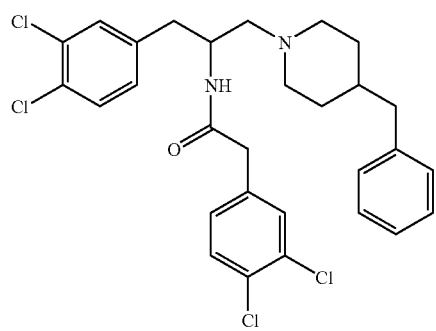
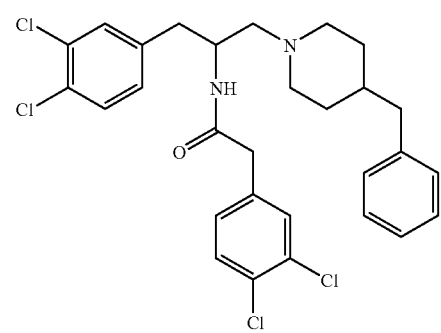
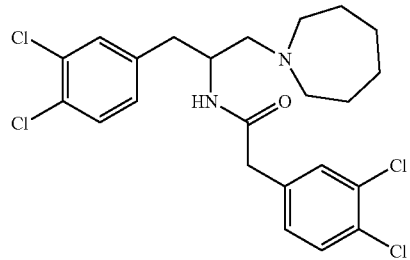
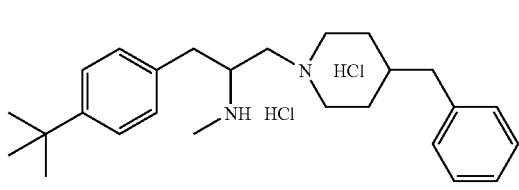

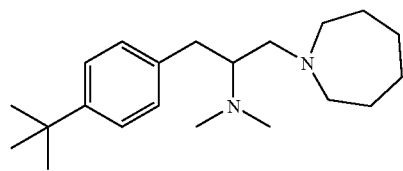
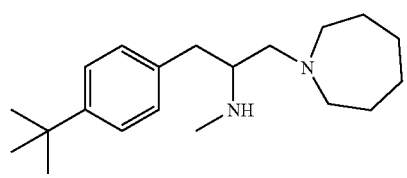
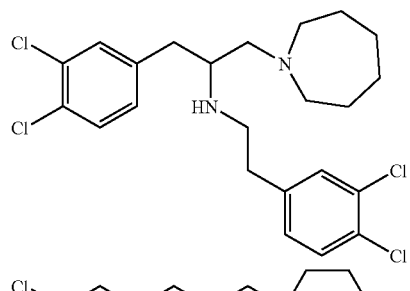
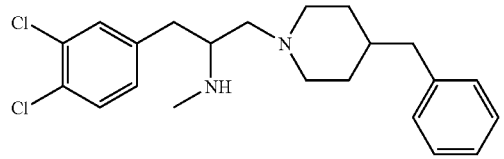
-continued
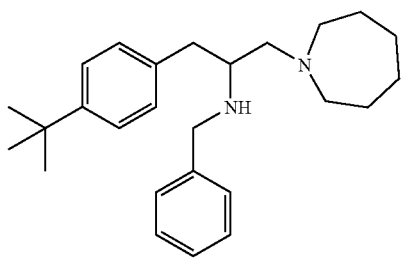
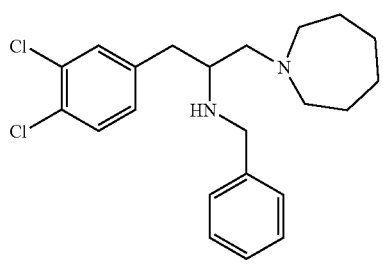
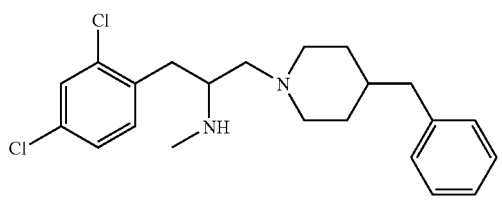
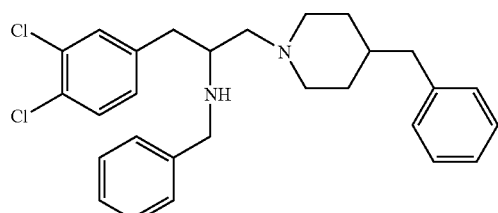
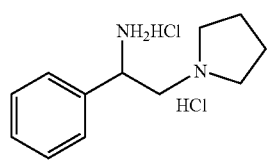
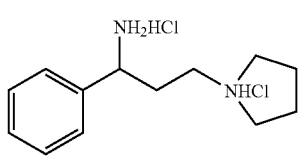
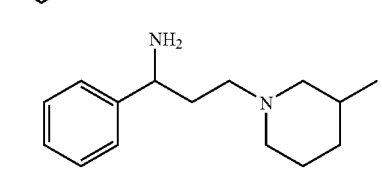
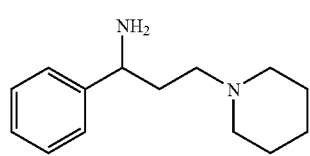
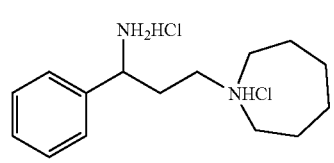
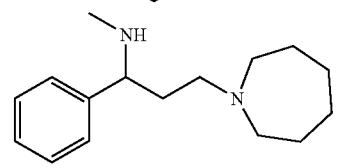
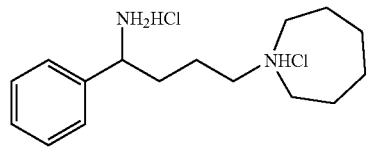
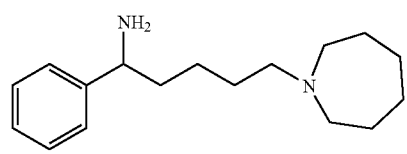
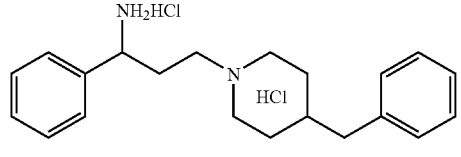
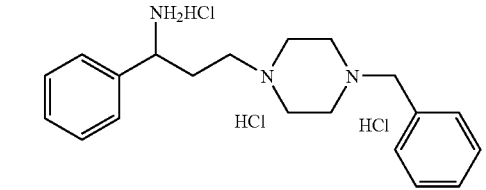

-continued
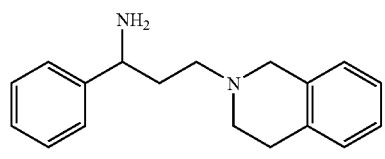
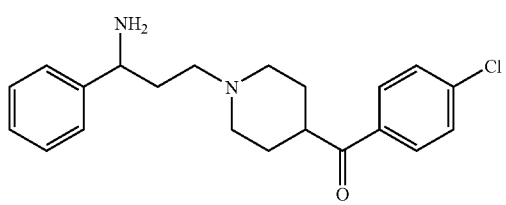
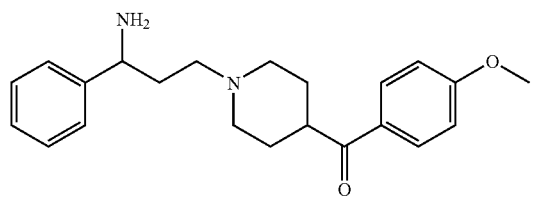
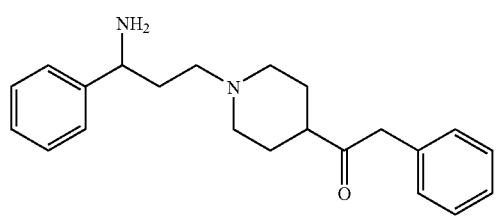
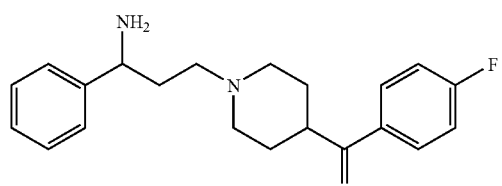
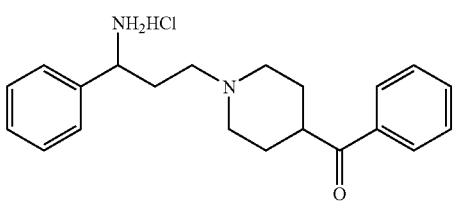
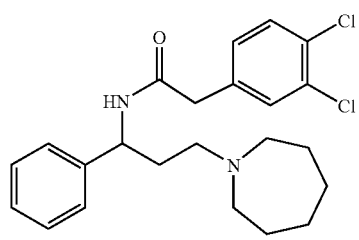
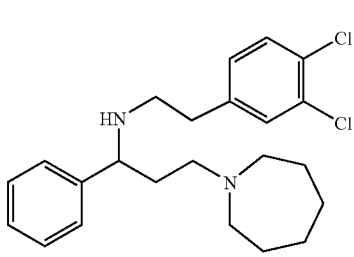
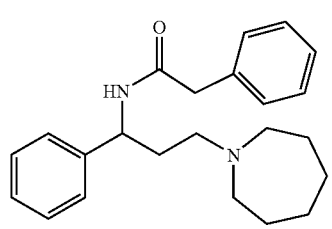
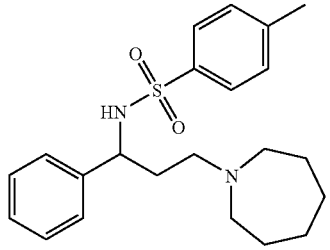
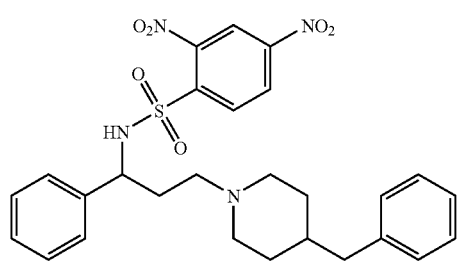
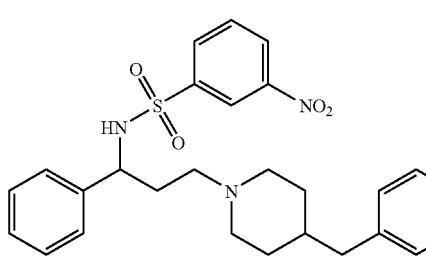
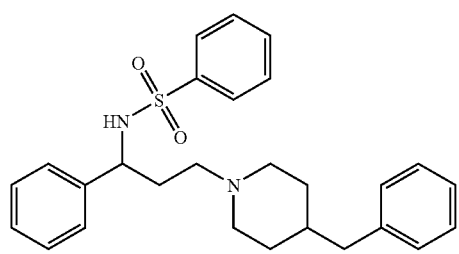
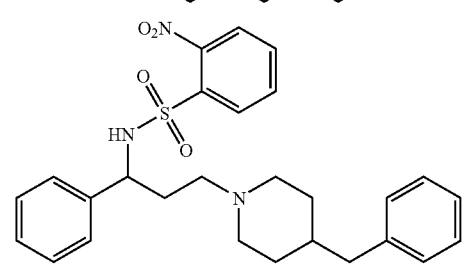

-continued
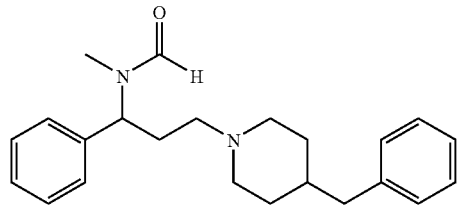
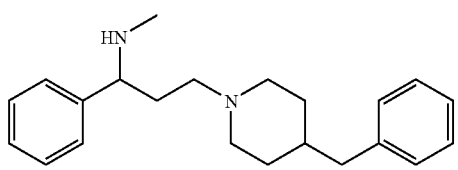
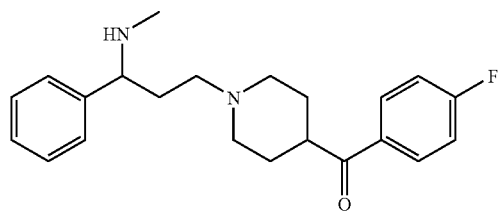
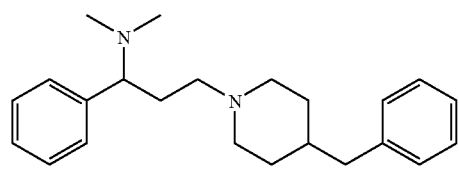
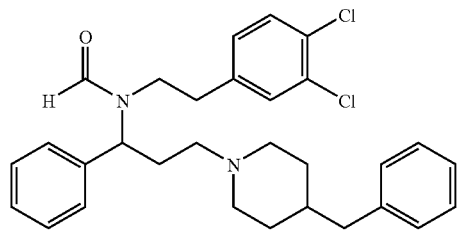
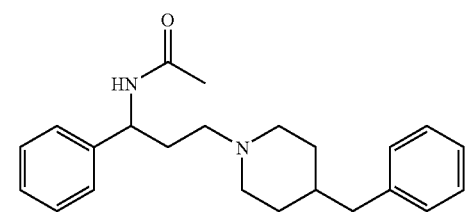
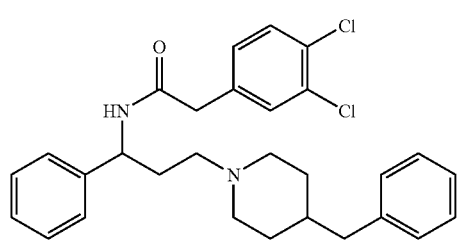
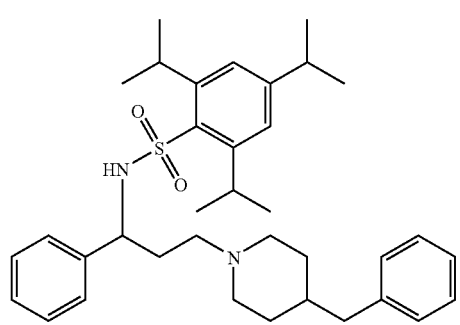
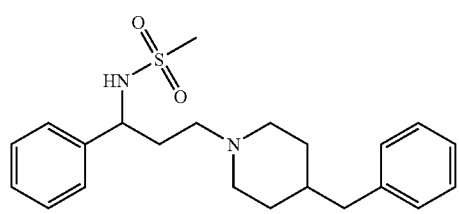
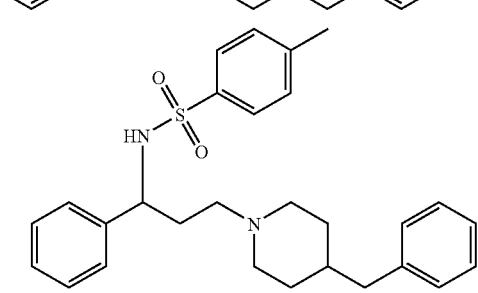
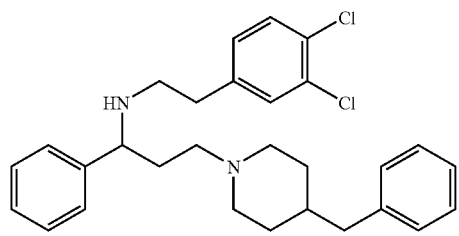
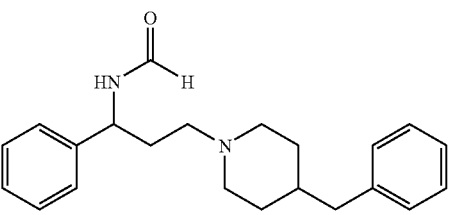

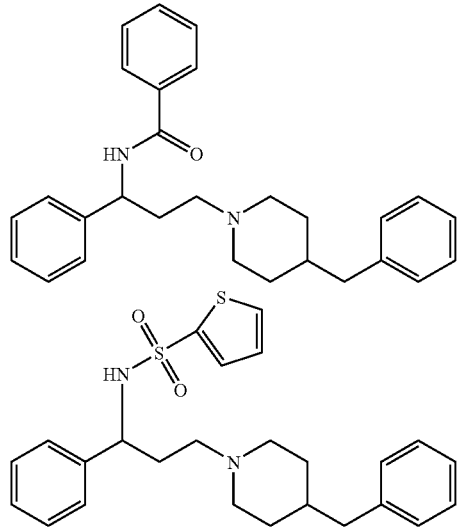

-continued

Materials and Methods

Sigma-1 and Sigma-2 Binding Assay Methods

Compounds of the present inventions were tested for selective binding to the sigma-1 receptor and sigma-2 receptor as modified from Chaki et al. Eur. J. Pharmacol. 1994, 251, $R_1$. and Akunne et al., Neuropharmacology, 1997, 36(1), 51.

Tissue Homogenate Preparation for Sigma-1 Binding Assay and Sigma-2 Binding Assay Male Hartley guinea pigs each weighing 300–400 g were used in sigma subtype binding assay. Guinea pigs were killed by decapitation and their whole brains (without cerebellum) were rapidly removed and homogenized in 25 volumes(W/V) of ice-cold 50 mM Tris-HCl buffer(pH 7.4 buffer for sigma-1 binding assay and pH 8.0 buffer for sigma-2 binding assay). The homogenate was centrifuged in 48,000×g for 10 min at 4° C. The supernatant was discarded and the resulting pellets were resuspended in the sane volume of buffer and recentrifuged as described above. The pellets were resuspended and washed twice more in the same manner as described above. The final pellets were resuspended in 10 volumes(W/V) of ice-cold 50 mM Tris-HCl buffer to enable distribution of 2 ml aliquot in microcentrifuge tube, which were used immediately or kept at −80° C. for no more than 1 month before use.

Sigma-1 Binding Assay ($[^3H](+)$pentazocine)

The sigma-1 selective binding assay was performed using $[^3H](+)$-pentazocine as the radioligand (2.4 nM final concentration unless otherwise specified) and approximately 127.5 pg of guinea pig brain membranes in a final volume of 500° of 50 mM TRISHCl, pH7.4. Non-specific binding was determined in the presence of 10° haloperidol. For the standard equilibrium assay, the mixtures were incubated for 2 hours at 25°, and rapidly filtered over Whatman GF/C glass fiber filters, followed by three 4.5 ml rinses with ice-cold incubation buffer. The filters were placed in counting vials and 4 ml scintillation solution. The vials were counted in a Beckman scintillation counter.

Sigma-2 Binding Assay($[^3H]$DTG)

The Sigma-2 selective binding assay was performed using 3.6 nM$[^3H]$DTG as the radioligand in the presence of 200 nM (+)-SKF10047 to block the Sigma-1 sites, with 168.8° of guinea pig brain membranes in a total volume of 0.5 ml of 50 mM TRIS-HCl, pH8.0. Non-specific binding was determined in the presence of 10° haloperidol. Incubation condition and other manipulations were as described above for sigma-1 binding assay.

IC50 values for sigma-1 or -2 binding assay were calculated using KELL RADLIG v.6.0.5.

TABLE I

| Structure | Sigma 1 IC50 (nM) | Sigma 2 Inhib. %[1] |
|---|---|---|
| (4-tert-butylbenzyl compound with azepane and NH₂·HCl) | 2.1 | 55.7 |
| (4-CF₃-benzyl compound with azepane and NH₂·HCl) | 2.0 | 43.9 |

TABLE I-continued
| Structure | Sigma 1 IC50 (nM) | Sigma 2 Inhib. %[1] |
|---|---|---|
| 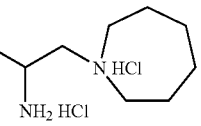 | 13.9 | 36.8 |
| 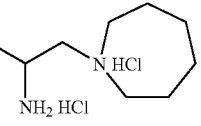 | 12.1 | 12.5 |
| 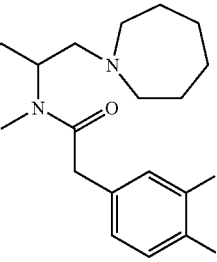 | 35.7 | 51.4 |
| 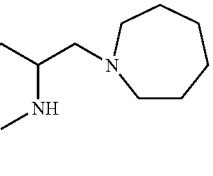 | 2.5 | 27.4 |
| 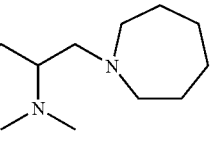 | 2.1 | ND |
| 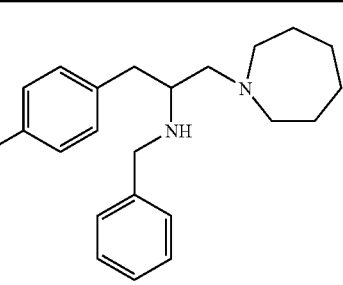 | 10.0 | ND |
| 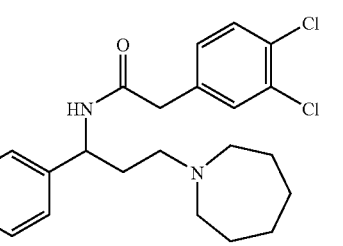 | 10.8 | 27.1 |
| 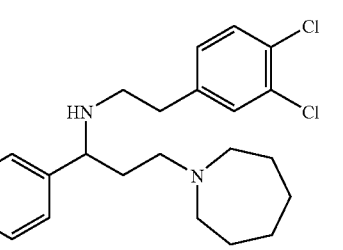 | 10.2 | 70.2 |
[1] Inhibition % at 10 nM.
ND = not determine
TABLE II
| Structure | Sigma 1 Inhib. %[1] | Sigma 2 Inhib. %[1] |
|---|---|---|
| 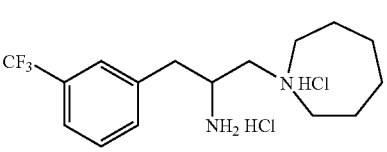 | 42.9 | 31.3 |
| 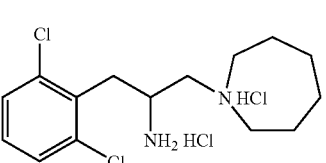 | 33.6 | 21.7 |

TABLE II-continued

| Structure | Sigma 1 Inhib. %[1] | Sigma 2 Inhib. %[1] |
|---|---|---|
| (2,4-dichlorobenzyl with CH(NH₂·HCl)-CH₂-N(HCl)-azepane) | 73.2 | 61.0 |
| (3,4-dichlorobenzyl with CH(NH₂·HCl)-CH₂-N(HCl)-4-benzylpiperidine) | 57.3 | 48.3 |
| (3,4-dichlorobenzyl with CH(NHCHO)-CH₂-N-4-benzylpiperidine) | 71.9 | 39.9 |
| (4-tert-butylbenzyl with CH(NH₂·HCl)-CH₂-N(HCl)-4-benzylpiperidine) | 26.1 | 38.2 |
| (3,4-dichlorobenzyl with CH(NHMe)-CH₂-N-4-benzylpiperidine) | 66.1 | 72.7 |
| (4-tert-butylbenzyl with CH(NHCHO)-CH₂-N-4-benzylpiperidine) | 52.7 | 6.1 |
| (2,4-dichlorobenzyl with CH(NH₂·HCl)-CH₂-N(HCl)-4-benzylpiperidine) | 56.9 | 48.3 |
| (4-tert-butylbenzyl with CH(NHMe·HCl)-CH₂-N(HCl)-4-benzylpiperidine) | 63.2 | 57.9 |

TABLE II-continued

| Structure | Sigma 1 Inhib. %[1] | Sigma 2 Inhib. %[1] |
|---|---|---|
| 2,4-dichlorobenzyl-CH(NHCHO)-CH2-N(4-benzylpiperidine) | 74.5 | 24.3 |
| 2,4-dichlorobenzyl-CH(NHCH3)-CH2-N(4-benzylpiperidine) | 75.6 | 75.0 |
| 3,4-dichlorobenzyl-CH(NHCHO)-CH2-N(azepane) | 67.7 | 37.8 |
| 2,4-dichlorobenzyl-CH(NH2·HCl)-CH2-N(HCl)(4-benzoylpiperidine) | 15.3 | 34.7 |
| 4-chlorobenzyl-CH(NH2)-CH2-N(4-benzoylpiperidine) | 38.9 | 50.0 |
| benzyl-C*H(NH2)-CH2-N(4-benzoylpiperidine) | 11.2 | 16.9 |
| benzyl-CH(NH2)-CH2-N(4-benzoylpiperidine) (racemic) | 33.6 | 34.0 |
| benzyl-C*H(NH2)-CH2-N(4-benzoylpiperidine) | 39.8 | 33.3 |

TABLE II-continued

| Structure | Sigma 1 Inhib. %[1] | Sigma 2 Inhib. %[1] |
| --- | --- | --- |
| (benzyl-CH(NH2)-CH2-N-piperidine-C(O)-CH2-phenyl) | 43.1 | 21.4 |
| (benzyl-CH(NH2)-CH2-N-piperidine-C(O)-4-Cl-phenyl) | 61.0 | 53.6 |
| (benzyl-CH(NH2)-CH2-N-piperidine-C(O)-4-F-phenyl) | 66.7 | 61.1 |
| (benzyl-CH(NH2)-CH2-N-piperidine-C(O)-3,4-diCl-phenyl) | 60.8 | 56.6 |
| (4-Cl-benzyl-CH(NH2)-CH2-N-piperidine-C(O)-4-Cl-phenyl) · 2HCl | 23.5 | 34.9 |
| (4-Cl-benzyl-CH(NH2)-CH2-N-piperidine-C(O)-4-F-phenyl) | 31.1 | 48.5 |
| (4-Cl-benzyl-CH(NH2)-CH2-N-piperidine-C(O)-3,4-diCl-phenyl) | 24.7 | 51.7 |
| (3,4-diCl-benzyl-CH(NH2)-CH2-N-piperidine-C(O)-phenyl) | 10.8 | 39.6 |
| (3,4-diCl-benzyl-CH(NH2)-CH2-N-piperidine-C(O)-3,4-diCl-phenyl) | 10.7 | 47.2 |

TABLE II-continued

| Structure | Sigma 1 Inhib. %[1] | Sigma 2 Inhib. %[1] |
|---|---|---|
| (structure) | 49.1 | 39.8 |
| (structure) | 19.5 | 31.0 |
| (structure) | 82.9 | 73.0 |
| (structure) | 34.5 | 41.6 |
| (structure) | 66.2 | 43.1 |
| (structure) | 47.4 | 30.0 |
| (structure) | 25.5 | 39.7 |
| (structure) | 7.1 | 21.6 |
| (structure) | 9.3 | 32.5 |

TABLE II-continued

| Structure | Sigma 1 Inhib. %[1] | Sigma 2 Inhib. %[1] |
|---|---|---|
| *3,4-dichlorophenethylamino compound with benzylpiperidine* | 28.8 | 22.6 |
| *N-formyl amino compound with benzylpiperidine* | 28.2 | 26.3 |
| *N-methylamino compound with benzylpiperidine* | 36.3 | 54.1 |
| *N-methyl-N-formyl compound with benzylpiperidine* | −2.0 | 26.4 |
| *N,N-dimethylamino compound with benzylpiperidine* | 20.3 | 57.7 |
| *Phenylsulfonamide compound with benzylpiperidine* | 35.6 | 11.4 |
| *2,4-dinitrophenylsulfonamide compound with benzylpiperidine* | 5.7 | 40.6 |

TABLE II-continued

| Structure | Sigma 1 Inhib. %[1] | Sigma 2 Inhib. %[1] |
|---|---|---|
| (3-nitrophenyl sulfonamide of 1-phenyl-3-(4-benzylpiperidin-1-yl)propylamine) | 45.7 | 25.7 |
| (2-nitrophenyl sulfonamide of 1-phenyl-3-(4-benzylpiperidin-1-yl)propylamine) | 31.6 | 3.1 |
| (benzamide of 1-phenyl-3-(4-benzylpiperidin-1-yl)propylamine) | 44.3 | 5.2 |
| (1-phenyl-3-(4-benzoylpiperidin-1-yl)propylamine·2HCl) | 13.7 | 48.3 |
| (1-phenyl-3-(4-(4-fluorobenzoyl)piperidin-1-yl)propylamine) | −1.9 | 57.3 |
| (1-phenyl-3-(4-phenylacetylpiperidin-1-yl)propylamine) | 2.2 | 28.7 |

TABLE II-continued

| Structure | Sigma 1 Inhib. %[1] | Sigma 2 Inhib. %[1] |
|---|---|---|
| (structure: 4-tert-butylbenzyl chain with NH2, linked to piperidine-CH2-phenyl) | 3.7 | 24.3 |
| (structure: HN-methyl, phenyl, propyl chain to piperidine with 4-fluorobenzoyl) | 25.2 | 50.5 |
| (structure: NH2, phenyl, propyl chain to piperidine with 4-methoxybenzoyl) | 3.2 | 30.9 |
| (structure: NH2, phenyl, propyl chain to piperidine with 4-chlorobenzoyl) | 7.9 | 43.7 |

[1] inhibition % at 10 nM

As described hereinbefore, the cyclic diamine compounds having the general formula I, III and IV of the present invention were observed to have high binding affinity at sigma receptor. Accordingly, the cyclic diamine compounds of the present invention having the general formula I, III and IV can be used in the treatment of CNS disorders including anxiety, psychosis, epilepsy, convulsion, movement disorders, motor disturbances, amnesia, cerebravascular diseases, senile dementia, e.g. of the Alzheimer type, and Parkinson's disease.

For therapeutic use in medicines, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and of optimum dosages for a particular situation must clinically be done and is within the skill of the art.

In utilizing the compounds of the present invention for the central nervous system, it is preferred to administer the compounds orally. Since the compounds absorb well orally, it usually will not be necessary to resort to parenteral administration. For oral administration, the compounds having the general formula I, III and IV are preferably combined with a pharmaceutical carrier. The ratio of the carrier to the compound of Structural Formula I, III and IV is not critical to express the effects of the medicine on the central nervous system, and they can vary considerably depending on whether the composition is to be filled into capsules or formed into tablets. Various edible pharmaceutical carriers or the mixture thereof can be used with the tablet form. Suitable carriers, for example, are a mixture of lactose, diabasic calcium phosphate and/or corn starch. Other pharmaceutically acceptable ingredients can be added, including lubricants such as magnesium stearate.

The present invention further includes compositions comprising Structural Formula I, III, IV. Furthermore, the present invention includes uses of the Epr compound I, III, IV and/or the composition.

A better understanding of the present invention may be obtained in light of following examples which are set forth to illustrate, but are not to be construed to limit, the present invention.

EXAMPLES

Example 1

1-Bromo-2-(tert-butoxycarbonyl)amino-3-phenyl propane

To a solution of the N-tert-butoxycarbonyl phenyl alaninol (1.42 mmol) and triphenylphosphine (2 equiv) in DMF, N-bromosuccinimide (2 equiv) was slowly added. The reaction was warmed to 50° for 15 min and then cooled to 20°. Methanol (0.5 mL) was added to destroy the excess reagent. After 5 min, ether was added, and the ether layer was washed with water, saturated sodium carbonate, and saturated NaCl and then evaporated to a solid under high vacuum. The product was extracted twice into hexane, leaving a residue of triphenylphosphine oxide. After evaporation of the solvent, the residue was again triturated with hexane to afford the 1-Bromo-2-(tert-butoxycarbonyl)amino-3-phenyl propane:
Yield 85%

Example 2 d-1-Benzyl-2-(1-hexamethyleneimino)ethylamine dihydrochloride

To a solution of d-1-Bromo-2-(tert-butoxycarbonyl)amino-3-phenyl propane (2 mmol) and potassium carbonate (2 equiv) in toluene (50 mL), hexamethyleneimine (1.1 equiv) was added and the mixture was refluxed for 24 h. The reaction mixture was filtered and the filtrate was washed with water, saturated solution of sodium hydrogen carbonate, dried (MgSO$_4$) and concentrated in vacuo. The residue was purified by column chromatography, eluting with an increasing ratio of ethyl acetate in hexane.

The resulting product was dissolved in 6% HCl-MeOH solution and allowed to stir for 2 h. The solvent was removed under reduced pressure and tritulated with THF to afford d-1-benzyl-2-(1-hexamethyleneimino)ethylamine dihydrochloride:
Yield 50% 1H-NMR(DMSO-D6, 200 MHz), •1.61(m, 4H), 1.81(m,4H), 2.92(m,2H), 3.23(m,6H), 4.05(m,1H), 7.36(s,5H), 8.83(br,3H), 10.79(br,1H)

Example 3 d-1-Benzyl-2-(1-morpholino)ethylamine dihydrochloride

The procedure given in Example 2 was followed using morpholine as a reactant, instead of hexamethyleneimine to give d-1-benzyl-2-(1-morpholino)ethylamine dihydrochloride.
1H-NMR(DMSO-D6, 200 MHz), •2.98(t,2H), 3.21(d, 3H), 3.39(q,2H), 3.61(m,1H), 3.87(s,4H), 4.13(m,1H), 7.33 (s,5H), 8.81(br,3H), 11.31(br,1H)

Example 4 d-1-Benzyl-2-(1-pyrrolidinyl)ethylamine dihydrochloride

The procedure given in Example 2 was followed using pyrrolidine as a reactant, instead of hexamethyleneimine to give d-1-benzyl-2-(1-pyrrolidinyl)ethylamine dihydrochloride.
1H-NMR(DMSO-D6, 200 MHz), •1.89(t,4H), 3.08(m, 1H), 3.20(m,3H), 3.41(m,1H), 3.60(m,3H), 3.94(m,1H), 7.32(s,5H), 8.87(br,3H), 11.11(br,1H)

Example 5 l-1-Benzyl-2-(N-succinimidyl)ethylamine hydrochloride

The procedure given in Example 2 was followed using l-1-bromo-2-(tert-butoxycarbonyl)amino-3-phenyl propane and succinimide as reactants, instead of d-1-Bromo-2-(tert-butoxycarbonyl)amino-3-phenyl propane and hexamethyleneimine to give l-1-benzyl-2-(N-succinimidyl)ethylamine hydrochloride.
1H-NMR(DMSO-D6, 200 MHz), •2.50(s,4H), 2.79(m, 1H), 3.17(d,1H), 3.40(m,1H), 3.64(d,2H), 7.29(s,5H), 8.41 (br,3H)

Example 6 l-1Benzyl-2-(1-pyrrolidinyl)ethylamine dihydrochloride

The procedure given in Example 2 was followed using l-1-Bromo-2-(tert-butoxycarbonyl)amino-3-phenyl propane and pyrrolidine as reactants, instead of d-1-bromo-2-(tert-butoxycarbonyl)amino-3-phenyl propane and hexamethyleneimine to give l-1-benzyl-2-(1-pyrrolidinyl)ethylamine dihydrochloride.
1H-NMR(DMSO-D6, 200 MHz), •1.89(t,4H), 3.08(m, 1H), 3.20(m,3H), 3.41(m,1H), 3.60(m,3H), 3.94(m,1H), 7.32(s,5H), 8.88(br,3H), 11.15(br,1H)

Example 7 d-1-Benzyl-2-(1-piperidinyl)ethylamine dihydrochloride

The procedure given in Example 2 was followed using piperidine as a reactant, instead of hexamethyleneimine to give d-1-benzyl-2-(1-piperidinyl)ethylamine dihydrochloride.
1H-NMR(DMSO-D6, 200 MHz), •1.34(m,1H), 1.75(m, 5H), 2.91(m,1H), 3.09(m,3H), 3.59(m,1H), 4.13(m,1H), 7.32(s,5H), 8.77(br,3H), 10.57(br,1H)

Example 8

1-Benzyl-2-(1-pyrrolidinyl)ethylamine dihydrochloride

The procedure given in Example 2 was followed using 1-bromo-2-(tert-butoxycarbonyl)amino-3-phenyl propane and pyrrolidine as reactants, instead of d-1-bromo-2-(tert-butoxycarbonyl)amino-3-phenyl propane and hexamethyleneimine to give 1-benzyl-2-(1-pyrrolidinyl)ethylamine dihydrochloride.
1H-NMR(DMSO-D6, 200 MHz), •1.89(t,4H), 3.08(m, 1H), 3.20(m,3H), 3.41(m,1H), 3.60(m,3H), 3.94(m,1H), 7.32(s,5H), 8.88(br,3H), 11.15(br,1H)

Example 9

1-(3,4-dichlorobenzyl)-2-(1-pyrrolidinyl)ethylamine dihydrochloride

The procedure given in Example 2 was followed using 1-bromo-2-(tert-butoxycarbonyl)amino-3-(3,4-dichloro)phenyl propane and pyrrolidine as reactants, instead of d-1-Bromo-2-(tert-butoxycarbonyl)amino-3-phenyl propane and hexamethyleneimine to give 1-(3,4-dichlorobenzyl)-2-(1-pyrrolidinyl)ethylamine dihydrochloride.

1H-NMR(DMSO-D6, 200 MHz), •1.95(m,4H), 3.13(m, 4H), 3.50(m,4H), 3.99(m,1H), 7.40(d,1H), 7.65(d,1H), 7.73 (s,1H), 8.71(br,3H), 11.11(br,1H)

Example 10

1-(4-chlorobenzyl)-2-(1-pyrrolidinyl)ethylamine dihydrochloride

The procedure given in Example 2 was followed using 1-bromo-2-(tert-butoxycarbonyl)amino-3-(4-chloro)phenyl propane and pyrrolidine as reactants, instead of d-1-bromo-2-(tert-butoxycarbonyl)amino-3-phenyl propane and hexamethyleneimine to give 1-(4-chlorobenzyl)-2-(1-pyrrolidinyl)ethylamine dihydrochloride.

1H-NMR(DMSO-D6, 200 MHz), •1.98(m,4H), 3.12(t, 3H), 3.34(t,2H), 3.58(t,3H), 3.97(m,1H), 7.46(s,4H), 8.75 (br,3H), 11.16(br,1H)

Example 11

1-(3-Chlorobenzyl)-2-(1-hexamethyleneimino)ethylamine dihydrochloride

The procedure given in Example 2 was followed using 1-bromo-2-(tert-butoxycarbonyl)amino-3-(3-chloro)phenyl propane as a reactant, instead of d-1-Bromo-2-(tert-butoxycarbonyl)amino-3-phenyl propane to give 1-(3-chlorobenzyl)-2-(1-hexamethyleneimino)ethylamine dihydrochloride.

1H-NMR(DMSO-D6, 200 MHz), •1.64(m,4H), 1.85(m, 4H), 3.03(m,4H), 3.25(m,4H), 4.10(m,1H), 7.41(s,3H), 7.55 (s,1H), 8.77(br,3H), 10.79(br,1H)

Example 12

1-[4-(Tert-butyl)benzyl]-2-(l-hexamethyleneimino)ethylamine dihydrochloride

The procedure given in Example 2 was followed using 1-bromo-2-(tert-butoxycarbonyl)amino-3-(4-tert-butyl)phenyl propane as a reactant, instead of d-1-bromo-2-(tert-butoxycarbonyl)amino-3-phenyl propane to give 1-[4-(tert-butyl)benzyl]-2-(1-hexamethyleneimino)ethylamine dihydrochloride.

1H-NMR(DMSO-D6, 200 MHz), •1.27(s,9H), 1.56(m, 4H), 1.80(m,4H), 2.97(q,2H), 3.21(m,4H), 3.50(m,2H), 4.05 (m,1H), 7.36(d,4H), 8.98(br,3H), 10.88(br,1H)

Example 13

1-[4-(Trifluoromethyl)benzyl]-2-(1-hexamethyleneimino)ethylamine dihydrochloride

The procedure given in Example 2 was followed using 1-bromo-2-(tert-butoxycarbonyl)amino-3-(4-trifluoromethyl)phenyl propane as a reactant, instead of d-1-bromo-2-(tert-butoxycarbonyl)amino-3-phenyl propane to give 1-[4-(trifluoromethyl)benzyl]-2-(1-hexamethyleneimino)ethylamine dihydrochloride.

1H-NMR(DMSO-D6, 200 MHz), •1.60(m,4H), 1.81(m, 4H), 3.16(m,4H), 3.32(m,4H), 4.14(m,1H), 7.69(d,4H), 8.86 (br,3H), 10.81(br,1H)

Example 14

1-(4-Chlorobenzyl)-2-(1-hexamethyleneimino)ethylamine dihydrochloride

The procedure given in Example 2 was followed using 1-bromo-2-(tert-butoxycarbonyl)amino-3-(4-chloro)phenyl propane as a reactant, instead of d-1-Bromo-2-(tert-butoxycarbonyl)amino-3-phenyl propane to give 1-(4-chlorobenzyl)-2-(1-hexamethyleneimino)ethylamine dihydrochloride.

1H-NMR(DMSO-D6, 200 MHz), •1.60(m,4H), 1.80(m, 4H), 3.05(m,2H), 3.21(m,4H), 3.48(m,2H), 4.05(m,1H), 7.39(s,4H), 8.84(br,3H), 10.79(br,1H)

Example 15

1-(3,4-Dichlorobenzyl)-2-(l-hexamethyleneimino)ethylamine dihydrochloride

The procedure given in Example 2 was followed using 1-bromo-2-(tert-9 butoxycarbonyl)amino-3-(3,4-dichloro)phenyl propane as a reactant, instead of d-1-Bromo-2-(tert-butoxycarbonyl)amino-3-phenyl propane to give 1-(3,4-dichlorobenzyl)-2-(1-hexamethyleneimino)ethylamine dihydrochloride.

1H-NMR(DMSO-D6, 200 MHz), •1.61(m,4H), 1.82(m, 4H), 3.04(m,2H), 3.25(m,4H), 3.52(m,2H), 4.08(m,1H), 7.39(s,1H), 7.65(d,2H), 8.81(br,3H), 10.83(br,1H)

Example 16

1-[3-(Trifluoromethyl)benzyl]-2-(l-hexamethyleneimino)ethylamine dihydrochloride

The procedure given in Example 2 was followed using 1-bromo-2-(tert-butoxycarbonyl)amino-3-(3-trifluoromethyl)phenyl propane as a reactant, instead of d-1-bromo-2-(tert-butoxycarbonyl)amino-3-phenyl propane to give 1-[3-(trifluoromethyl)benzyl]-2-(1-hexamethyleneimino)ethylamine dihydrochloride.

1H-NMR(DMSO-D6, 200 MHz), •1.58(m,4H), 1.81(m, 4H), 3.13(m,4H), 3.40(m,4H), 4.15(m,1H), 7.62(m,3H), 7.80(s,1H), 8.80(br,3H), 10.84(br,1H)

Example 17

1-(2,6-Dichlorobenzyl)-2-(1-hexamethyleneimino)ethylamine dihydrochloride

The procedure given in Example 2 was followed using 1-bromo-2-(tert-butoxycarbonyl)amino-3-(2,6-dichloro)phenyl propane as a reactant, instead of d-1-bromo-2-(tert-butoxycarbonyl)amino-3-phenyl propane to give 1-(2,6-dichlorobenzyl)-2-(1-hexamethyleneimino)ethylamine dihydrochloride.

1H-NMR(DMSO-D6, 200 MHz), •1.51(m,4H), 1.73(m, 4H), 3.05(m,2H), 3.21(m,4H), 3.42(m,1H), 3.69(m,1H), 3.98(m,1H), 7.39(m,1H), 7.51(m,2H), 9.12(br,3H), 10.77 (br,1H)

Example 18

1-(2-Methylbenzyl)-2-(1-hexamethyleneimino)ethylamine dihydrochloride

The procedure given in Example 2 was followed using 1-bromo-2-(tert-butoxycarbonyl)amino-3-(2-methyl)phenyl propane as a reactant, instead of d-1-bromo-2-(tert-butoxycarbonyl)amino-3-phenyl propane to give 1-(2-methylbenzyl)-2-(1-hexamethyleneimino)ethylamine dihydrochloride.

1H-NMR(DMSO-D6, 200 MHz), •1.55(m,4H), 1.75(m, 4H), 2.30(s,2H), 2.49(s,1H), 2.99(m,2H), 3.22(m,3H), 3.59 (m,3H), 3.99(m,1H), 6.99(s,2H), 7.31(m,2H), 9.05(br,3H), 10.83(br,1H)

Example 19

1-(3-Chlorobenzyl)-2-(1-pyrrolidinyl)ethylamine dihydrochloride

The procedure given in Example 2 was followed using 1-bromo-2-(tert-butoxycarbonyl)amino-3-(3-chloro)phenyl propane and pyrrolidine as a reactant, instead of d-1-bromo-2-(tert-butoxycarbonyl)amino-3-phenyl propane and hexamethyleneimine to give 1-(3-chlorobenzyl)-2-(1-pyrrolidinyl)ethylamine dihydrochloride.

1H-NMR(DMSO-D6, 200 MHz), •1.92(m,4H), 3.10(m, 2H), 3.50(m,2H), 3.61(m,4H), 3.98(m,1H), 7.35(s,3H), 7.51 (s,1H), 8.77(br,3H), 11.15(br,1H)

Example 20

1-[4-(Trifluoromethyl)benzyl]-2-(1-pyrrolidinyl)ethylamine dihydrochloride

The procedure given in Example 2 was followed using 1-bromo-2-(tert-butoxycarbonyl)amino-3-(4-trifluoromethyl)phenyl propane and pyrrolidine as a reactant, instead of d-1-bromo-2-(tert-butoxycarbonyl)amino-3-phenyl propane and hexamethyleneimine to give 1-[4-(trifluoromethyl)benzyl]-2-(1-pyrrolidinyl)ethylamine dihydrochloride.

1H-NMR(DMSO-D6, 200 MHz), •1.94(m,4H), 3.21(m, 2H), 3.57(m,6H), 4.05(m,1H), 7.69(d,4H), 8.82(br,3H), 11.19(br,1H)

Example 21

1-(2,4-Dichlorobenzyl)-2-(1-hexamethyleneimino)ethylamine dihydrochloride

The procedure given in Example 2 was followed using 1-bromo-2-(tert-butoxycarbonyl)amino-3-(2,4-dichloro)phenyl propane as a reactant, instead of d-1-bromo-2-(tert-butoxycarbonyl)amino-3-phenyl propane to give 1-(2,4-dichlorobenzyl)-2-(1-hexamethyleneimino)ethylamine dihydrochloride.

1H-NMR(DMSO-D6, 200 MHz), •1.59(m,4H), 1.78(m, 4H), 3.15(d,2H), 3.26(m,4H), 3.44(m,1H), 3.61(m,1H), 4.05 (m,1H), 7.53(q,2H), 7.69(s,1H), 6.80(br,3H), 10.74(br,1H)

Example 22

1-(Phenethyl)-2-(1-hexamethyleneimino)ethylamine dihydrochloride

The procedure given in Example 2 was followed using 1-bromo-2-(tert-butoxycarbonyl)amino-4-phenyl butane as a reactant, instead of d-1-bromo-2-(tert-butoxycarbonyl)amino-3-phenyl propane to give 1-(phenethyl)-2-(1-hexamethyleneimino)ethylamine dihydrochloride.

1H-NMR(DMSO-D6, 200 MHz), •1.61(m,4H), 1.87(m, 4H), 1.99(m,2H), 2.70(t,2H), 3.25(m,3H), 3.49(m,3H), 3.74 (m,1H), 7.22(m,5H), 8.76(br,3H), 10.79(br,1H)

Example 23

1-(3,4-Dichlorobenzyl)-2-[1-(4-benzylpiperidinyl)]ethylamine dihydrochloride

The procedure given in Example 2 was followed using 1-bromo-2-(tert-butoxycarbonyl)amino-3-(3,4-dichloro)phenyl propane and 4-benzylpiperidine as reactants, instead of d-1-bromo-2-(tert-butoxycarbonyl)amino-3-phenyl propane and hexamethyleneimine to give 1-(3,4-dichlorobenzyl)-2-[1-(4-benzylpiperidinyl)]ethylamine dihydrochloride.

1H-NMR(DMSO-D6, 200 MHz), •1.64(m,5H), 2.59(m, 2H), 3.18(m,4H), 3.41(m,4H), 4.15(m,1H), 7.12(m,5H), 7.53(q,3H), 7.64(s,1H), 8.89(br,3H), 10.61(br,1H)

Example 24

1-[4-(Tert-butyl)benzyl]-2-[1-(4-benzylpiperidinyl)lethylamine dihydrochloride

The procedure given in Example 2 was followed using 1-bromo-2-(tert-butoxycarbonyl)amino-3-(4-tert-butyl)phenyl propane and 4-benzylpiperidine as reactants, instead of d-1-bromo-2-(tert-butoxycarbonyl)amino-3-phenyl propane and hexamethyleneimine to give 1-[4-(tert-butyl)benzyl]-2-[1-(4-benzylpiperidinyl)]ethylamine dihydrochloride.

1H-NMR(DMSO-D6, 200 MHz), •1.21(s,9H), 1.71(m, 5H), 2.59(m,2H), 2.93(m,1H), 3.07(m,3H), 3.45(m,3H), 3.69(m,1H), 4.14(m,1H), 7.29(m,9H), 8.76(br,3H), 10.60 (br,1H)

Example 25

1-(2,4-Dichlorobenzyl)-2-[1-(4-benzylpiperidinyl)]ethylamine dihydrochloride

The procedure given in Example 2 was followed using 1-bromo-2-(tert-butoxycarbonyl)amino-3-(2,4-dichloro)phenyl propane and 4-benzylpiperidine as reactants, instead of d-1-bromo-2-(tert-butoxycarbonyl)amino-3-phenyl propane and hexamethyleneimine to give 1-(2,4-dichlorobenzyl)-2-[1-(4-benzylpiperidinyl)]ethylamine dihydrochloride.

1H-NMR(DMSO-D6, 200 MHz), •1.68(m,5H), 2.61(m, 2H), 3.18(m,4H), 3.43(m,3H), 3.62(m,1H), 4.12(m,1H), 7.20(m,5H), 7.54(q,2H), 7.69(s,1H), 8.83(br,3H), 10.53(br, 1H)

Example 26

1-(4-Chlorobenzyl)-2-[1-(4-benzoylpiperidinyl)]ethylamine

The procedure given in Example 2 except for the formation of salts was followed using 1-bromo-2-(tert-butoxycarbonyl)amino-3-(4-chloro)phenyl propane and 4-benzoylpiperidine as reactants, instead of d-1-bromo-2-(tert-butoxycarbonyl)amino-3-phenyl propane and hexamethyleneimine to give 1-(4-chlorobenzyl)-2-[1-(4-benzoylpiperidinyl)]ethylamine.

1H-NMR(CDCl₃, 200 MHz), •2.78(m,5H), 2.03(m,2H), 2.28(m,3H), 2.51(m,1H), 2.68(m,1H), 2.96(m,2H), 3.21(m, 2H), 7.19(q,2H), 7.22(s,3H), 7.48(q,2H), 7.93(d,2H)

Example 27

1-[4-(Tert-butyl)benzyl]-3-[1-(4-benzoylpiperidinyl)]propylamine

The procedure given in Example 2 except for the formation of salts was followed using 1-bromo-2-(tert-butoxycarbonyl)amino-3-(4-tert-butyl)phenyl propane and 4-benzoylpiperidine as reactants, instead of d-1-bromo-2-(tert-butoxycarbonyl)amino-3-phenyl propane and hexamethyleneimine to give 1-[4-(tert-butyl)benzyl]-3-[1-(4-benzoylpiperidinyl)]propylamine.

1H-NMR(CDCl₃, 200 MHz), •1.20(s,9H), 1.89(m,6H), 2.31(m,1H), 2.59(m,2H), 2.92(m,2H), 3.23(m,4H), 3.65(m, 1H), 6.57(br,2H), 7.16(d,2H), 7.30(d,2H), 7.47(m,3H), 7.88 (d,2H)

Example 28

1-[4-(Tert-butyl)benzyl]-3-[1-(4-(phenylacetyl)piperidinyl)]propylamine

The procedure given in Example 2 except for the formation of salts was followed using 1-bromo-2-(tert-butoxycarbonyl)amino-3-(4-tert-butyl)phenyl propane and 4-(phenylacetyl)piperidine as reactants, instead of d-1-bromo-2-(tert-butoxycarbonyl)amino-3-phenyl propane and hexamethyleneimine to give 1-[4-(tert-butyl)benzyl]-3-[1-(4-(phenylacetyl)piperidinyl)]propylamine.

1H-NMR(CDCl₃, 200 MHz), •1.22(s,9H), 1.76(m,6H), 1.99(m,2H), 2.47(m,2H), 2.84(m,3H), 3.18(m,2H), 3.70(s, 2H), 5.00(br,3H), 7.12(m,4H), 7.28(m,5H)

Example 29

1-[4-(Tert-butyl)benzyl]-3-[1-(4-benzylpiperidinyl)]propylamine

The procedure given in Example 2 except for the formation of salts was followed using 3-bromo-1-(tert-butoxycarbonyl)amino-1-(4-tert-butyl)benzyl propane and 4-benzylpiperidine as reactants, instead of d-1-Bromo-2-(tert-butoxycarbonyl)amino-3-phenyl propane and hexamethyleneimine to give 1-[4-(tert-butyl)benzyl]-3-[1-(4-benzylpiperidinyl)]propylamine.

1H-NMR(CDCl₃, 200 MHz), •1.23(s,9H), 1.65(m,5H), 2.03(m,2H), 2.49(m,4H), 2.89(m,4H), 3.19(m,2H), 5.55(br, 3H), 7.11(m,4H), 7.26(m,5H)

Example 30 d-1-Benzyl-2-[1-(4-benzoylpiperidinyl)]ethylamine

The procedure given in Example 2 except for the formation of salts was followed using 4-benzoylpiperidine as a reactant, instead of hexamethyleneimine to give d-1-benzyl-2-[1-(4-benzoylpiperidinyl)]ethylamine.

1H-NMR(CDCl₃, 200 MHz), •1.85(m,4H), 2.17(m,6H), 2.35(m,2H), 2.95(m,2H), 3.25(m,2H), 7.25(m,5H), 7.49(q, 3H), 7.93(d,2H)

Example 31

1-Benzyl-2-[1-(4-benzoylpiperidinyl)]ethylamine

The procedure given in Example 2 except for the formation of salts was followed using 1-bromo-2-(tert-butoxycarbonyl)amino-3-phenyl propane and 4-benzoylpiperidine as reactants, instead of d-1-bromo-2-(tert-butoxycarbonyl)amino-3-phenyl propane and hexamethyleneimine to give 1-benzyl-2-[1-(4-benzoylpiperidinyl)]ethylamine.

1H-NMR(CDCl₃, 200 MHz), •1.85(m,4H), 2.17(m,6H), 2.35(m,2H), 2.98(m,2H), 3.29(m,2H), 7.25(m,5H), 7.49(q, 3H), 7.93(d,2H)

Example 32 l-1-Benzyl-2-[1-(4-benzoylpiperidinyl)]ethylamine

The procedure given in Example 2 except for the formation of salts was followed using l-1-bromo-2-(tert-butoxycarbonyl)amino-3-phenyl propane and 4-benzoylpiperidine as reactants, instead of d-1-bromo-2-(tert-butoxycarbonyl)amino-3-phenyl propane and hexamethyleneimine to give l-1-benzyl-2-[1-(4-benzoylpiperidinyl)]ethylamine.

1H-NMR(CDCl₃, 200 MHz), •1.85(m,4H), 2.17(m,6H), 2.35(m,2H), 2.98(m,2H), 3.38(m,2H), 7.25(m,5H), 7.49(q, 3H), 7.93(d,2H)

Example 33 l-1-Benzyl-2-[1-(4-(phenylacetyl)piperidinyl)]ethylamine

The procedure given in Example 2 except for the formation of salts was followed using l-1-bromo-2-(tert-butoxycarbonyl)amino-3-phenyl propane and 4-(phenylacetyl)piperidine as reactants, instead of d-1-bromo-2-(tert-butoxycarbonyl)amino-3-phenyl propane and hexamethyleneimine to give l-1-benzyl-2-[1-(4-(phenylacetyl)piperidinyl)]ethylamine.

1H-NMR(CDCl₃, 200 MHz), •1.77(m,9H), 2.35(m,4H), 2.91(m,2H), 3.11(m,1H), 3.70(s,2H), 7.18(t,4H), 7.25(t,6H)

Example 34 l-1-Benzyl-2-[1-(4-(4-chlorobenzoyl)piperidinyl)]ethylamine

The procedure given in Example 2 except for the formation of salts was followed using l-1-bromo-2-(tert-butoxycarbonyl)amino-3-phenyl propane and 4-(4-chlorobenzoyl)piperidine as reactants, instead of d-1-bromo-2-(tert-butoxycarbonyl)amino-3-phenyl propane and hexamethyleneimine to give l-1-benzyl-2-[1-(4-(4-chlorobenzoyl)piperidinyl)]ethylamine.

1H-NMR(CDCl₃, 200 MHz), •1.79(m,2H), 1.91(m,5H), 2.32(d,3H), 2.59(m,1H), 2.75(m,₁H), 2.99(m,2H), 3.20(q, 2H), 7.23(q,5H), 7.43(d,2H), 7.88(d,2H)

Example 35 l-1-Benzyl-2-[1-(4-(4-fluorobenzoyl)piperidinyl)]ethylamine

The procedure given in Example 2 except for the formation of salts was followed using l-1-bromo-2-(tert-butoxycarbonyl)amino-3-phenyl propane and 4-(4-fluorobenzoyl)

piperidine as reactants, instead of d-1-bromo-2-(tert-butoxycarbonyl)amino-3-phenyl propane and hexamethyleneimine to give l-1-benzyl-2-[1-(4-(4-fluorobenzoyl)piperidinyl)]ethylamine.

1H-NMR(CDCl$_3$, 200 MHz), •1.85(m,2H), 1.92(m,5H), 2.34(d,3H), 2.55(m,$_1$H), 2.74(m,1H), 2.99(m,2H), 3.22(q, 2H), 7.13(t,2H), 7.25(m,5H), 7.95(t,2H)

Example 36 l-1-Benzyl-2-[1-(4-(3,4-dichlorobenzoyl)piperidinyl)]ethylamine

The procedure given in Example 2 except for the formation of salts was followed using l-1-bromo-2-(tert-butoxycarbonyl)amino-3-phenyl propane and 4-(3,4-dichlorobenzoyl)piperidine as reactants, instead of d-1-bromo-2-(tert-butoxycarbonyl)amino-3-phenyl propane and hexamethyleneimine to give l-1-benzyl-2-[1-(4-(3,4-dichlorobenzoyl)piperidinyl)]ethylamine.

1H-NMR(CDCl$_3$, 200 MHz), •1.82(m,4H), 1.95(s,3H), 2.33(d,3H), 2.58(m,1H), 2.74(m,1H), 2.99(m,2H), 3.19(m, 2H), 7.27(m,5H), 7.54(d,1H), 7.74(d,1H), 7.99(s,1H)

Example 37

1-(3,4-Dichlorobenzyl)-2-[1-(4-benzoylpiperidinyl)]ethylamine

The procedure given in Example 2 except for the formation of salts was followed using 1-bromo-2-(tert-butoxycarbonyl)amino-3-(3,4-dichloro)phenyl propane and 4-benzoylpiperidine as reactants, instead of d-1-bromo-2-(tert-butoxycarbonyl)amino-3-phenyl propane and hexamethyleneimine to give 1-(3,4-dichlorobenzyl)-2-[1-(4-benzoylpiperidinyl)]ethylamine.

1H-NMR(CDCl$_3$, 200 MHz), •1.81(m,4H), 1.94(s,2H), 2.06(m,1H), 2.30(d,3H), 2.66(d,2H), 2.94(t,2H), 3.25(t,2H), 7.07(d,1H), 7.31(t,2H), 7.47(m,3H), 7.90(d,2H)

Example 38

1-(4-Chlorobenzyl)-2-[1-(4-(3,4-dichlorobenzoyl)piperidinyl)]ethylamine

The procedure given in Example 2 except for the formation of salts was followed using 1-bromo-2-(tert-butoxycarbonyl)amino-3-(4-chloro)phenyl propane and 4-(3,4-dichlorobenzoyl)piperidine as reactants, instead of d-1-bromo-2-(tert-butoxycarbonyl)amino-3-phenyl propane and hexamethyleneimine to give 1-(4-chlorobenzyl)-2-[1-(4-(3,4-dichlorobenzoyl)piperidinyl)]ethylamine.

1H-NMR(CDCl$_3$, 200 MHz), •1.81(m,3H), 2.02(m,1H), 2.27(d,2H), 2.43(m,4H), 2.69(d,2H), 2.95(m,2H), 3.18(m, 2H), 7.16(d,2H), 7.23(d,2H), 7.57(d,1H), 7.75(d,1H), 8.00(s,1H)

Example 39

1-(3,4-Dichlorobenzyl)-2-[1-(4-(3,4-dichlorobenzoyl)piperidinyl)]ethylamine

The procedure given in Example 2 except for the formation of salts was followed using 1-bromo-2-(tert-butoxycarbonyl)amino-3-(3,4-dichloro)phenyl propane and 1-(4-chlorobenzyl)-2-[1-(4-(3,4-dichlorobenzoyl)-piperidinyl)]ethylamine as reactants, instead of d-1-bromo-2-(tert-butoxycarbonyl)amino-3-phenyl propane and hexamethyleneimine to give 1-(3,4-dichlorobenzyl)-2-[1-(4-(3,4-dichlorobenzoyl)piperidinyl)]ethylamine.

1H-NMR(CDCl$_3$, 200 MHz), •1.79(m,4H), 2.30(d,3H), 2.50(m,3H), 2.65(t,2H), 2.92(t,2H), 3.17(m,2H), 7.07(d, 1H), 7.31(t,2H), 7.53(d,1H), 7.73(d,1H), 7.98(s,1H)

Example 40 l-1-Benzyl-2-[1-(4-(4-methoxybenzoyl)piperidinyl)]ethylamine

The procedure given in Example 2 except for the formation of salts was followed using l-1-bromo-2-(tert-butoxycarbonyl)amino-3-phenyl propane and 4-(4-methoxybenzoyl)piperidine as reactants, instead of d-1-bromo-2-(tert-butoxycarbonyl)amino-3-phenyl propane and hexamethyleneimine to give l-1-benzyl-2-[1-(4-(4-methoxybenzoyl)piperidinyl)]ethylamine.

1H-NMR(CDCl$_3$, 200 MHz), •1.82(m,4H), 1.91(s,3H), 2.30(d,2H), 2.32(s,1H), 2.52(m,1H), 2.73(m,1H), 2.99(m, 2H), 3.20(m,2H), 3.89(s,3H), 6.94(d,2H), 7.21(m,5H), 7.92(d,2H)

Example 41

1-(4-Chlorobenzyl)-2-[1-(4-(4-methoxybenzoyl)piperidinyl)]ethylamine

The procedure given in Example 2 except for the formation of salts was followed using 1-bromo-2-(tert-butoxycarbonyl)amino-3-(4-chloro)phenyl propane and 4-(4-methoxybenzoyl)piperidine as reactants, instead of d-1-bromo-2-(tert-butoxycarbonyl)amino-3-phenyl propane and hexamethyleneimine to give 1-(4-chlorobenzyl)-2-[1-(4-(4-methoxybenzoyl)piperidinyl)]ethylamine.

1H-NMR(CDCl$_3$, 200 MHz), •1.91(m,4H), 2.00(s,3H), 2.28(d,3H), 2.51(m,1H), 2.71(m,1H), 2.97(m,2H), 3.20(m, 2H), 3.87(s,3H), 6.93(d,2H), 7.21(q,4H), 7.92(d,2H)

Example 42 l-1-Benzyl-2-[1-(4-(4-tert-butylbenzoyl)piperidinyl)]ethylamine

The procedure given in Example 2 except for the formation of salts was followed using l-1-bromo-2-(tert-butoxycarbonyl)amino-3-phenyl propane and 4-(4-tert-butylbenzoyl)piperidine as reactants, instead of d-1-bromo-2-(tert-butoxycarbonyl)amino-3-phenyl propane and hexamethyleneimine to give l-1-benzyl-2-[1-(4-(4-tert-butylbenzoyl)piperidinyl)]ethylamine.

1H-NMR(CDCl$_3$, 200 MHz), •1.32(s,9H), 1.83(m,4H), 2.22(m,3H), 2.34(m,3H), 2.58(m,1H), 2.74(m,1H), 2.98(m, 2H), 3.23(m,2H), 7.23(m,5H), 7.48(d,2H), 7.89(d,2H)

Example 43 l-1-[4-(Tert-butyl)benzyl]-2-[1-(4-benzoylpiperidinyl)]ethylamine

The procedure given in Example 2 except for the formation of salts was followed using 1-bromo-2-(tert-butoxycarbonyl)amino-3-(4-tert-butyl)phenyl propane and 4-benzoylpiperidine as reactants, instead of d-1-bromo-2-(tert-butoxycarbonyl)amino-3-phenyl propane and hexamethyleneimine to give 1-[4-(tert-butyl)benzyl]-2-[1-(4-benzoylpiperidinyl)]ethylamine.

1H-NMR(CDCl₃, 200 MHz), •1.28(s,9H), 1.83(m,4H), 2.21(m,3H), 2.33(m,3H), 2.53(m,1H), 2.72(m,1H), 2.99(m,2H), 3.22(m,2H), 7.14(d,2H), 7.32(d,2H), 7.49(m,3H), 7.92(d,2H)

Example 44

1-Phenyl-3-(1-hexamethyleneimino)-n-propylamine dihydrochloride

The procedure given in Example 2 was followed using 3-bromo-1-(tert-butoxycarbonyl)amino-1-phenyl propane as a reactant, instead of d-1-bromo-2-(tert-butoxycarbonyl)amino-3-phenyl propane to give 1-Phenyl-3-(1-hexamethyleneimino)-n-propylamine dihydrochloride.

1H-NMR(DMSO-D6, 200 MHz), •1.59(m,4H), 1.73(m,4H), 3.0(m,2H), 3.12(m,2H), 3.61(m,4H), 4.56(m,1H), 7.43(m,3H), 7.65(m,2H), 8.99(br,3H), 11.30(br,1H)

Example 45

1-Phenyl-2-(1-pyrrolidinyl)ethylamine dihydrochloride

The procedure given in Example 2 was followed using 1-bromo-2-(tert-butoxycarbonyl)amino-2-phenyl ethane and pyrrolidine as reactants, instead of d-1-bromo-2-(tert-butoxycarbonyl)amino-3-phenyl propane and hexamethyleneimine to give 1-Phenyl-2-(1-pyrrolidinyl)ethylamine dihydrochloride.

1H-NMR(DMSO-D6, 200 MHz), •1.92(t,4H), 3.41(t,4H), 3.65(m,1H), 4.05(m,1H), 4.98(m,1H), 7.48(m,3H), 7.71(m,2H), 9.28(br,3H), 11.14(br,1H)

Example 46

1-Phenyl-3-(1-pyrrolidinyl)-n-propylamine dihydrochloride

The procedure given in Example 2 was followed using 3-bromo-1-(tert-butoxycarbonyl)amino-1-phenyl propane and pyrrolidine as reactants, instead of d-1-bromo-2-(tert-butoxycarbonyl)amino-3-phenyl propane and hexamethyleneimine to give 1-Phenyl-3-(1-pyrrolidinyl)-n-propylamine dihydrochloride.

1H-NMR(DMSO-D6, 200 MHz), •1.95(t,4H), 3.0(m,2H), 3.12(m,2H), 3.61(m,4H), 4.56(m,1H), 7.43(m,3H), 7.65(m,2H), 9.00(br,3H), 11.38(br,1H)

Example 47

1-Phenyl-3-[1-(4-benzylpiperidinyl)]-n-propylamine dihydrochloride

The procedure given in Example 2 was followed using 3-Bromo-1-(tert-butoxycarbonyl)amino-1-phenyl propane and 4-benzylpiperidine as reactants, instead of d-1-Bromo-2-(tert-butoxycarbonyl)amino-3-phenyl propane and hexamethyleneimine to give 1-Phenyl-3-[1-(4-benzylpiperidinyl)]-n-propylamine dihydrochloride.

1H-NMR(DMSO-D6, 200 MHz), •1.69(m,4H), 1.78(m,4H), 2.79(m,2H), 3.11(m,2H), 3.59(m,3H), 4.42(m,1H), 7.20(m,5H), 7.40(s,3H), 7.58(s,2H), 8.81(br,3H), 10.78(br,1H)

Example 48

1-Phenyl-3-(1-piperidinyl)-n-propylamine

The procedure given in Example 2 except for the formation of salts was followed using 3-bromo-1-(tert-butoxycarbonyl)amino-1-phenyl propane and piperidine as reactants, instead of d-1-bromo-2-(tert-butoxycarbonyl)amino-3-phenyl propane and hexamethyleneimine to give 1-Phenyl-3-(1-piperidinyl)-n-propylamine.

1H-NMR(CDCl₃, 200 MHz), •1.39(m,2H), 1.52(m,4H), 1.81(q,2H), 2.10(t,2H), 2.31(m,6H), 3.92(t,1H), 7.21(m,5H)

Example 49

1-Phenyl-4-(1-hexamethyleneimino)-n-butylamine dihydrochloride

The procedure given in Example 2 was followed using 4-bromo-1-(tert-butoxycarbonyl)amino-1-phenyl butane as a reactant, instead of d-1-bromo-2-(tert-butoxycarbonyl)amino-3-phenyl propane to give 1-Phenyl-4-(1-hexamethyleneimino)-n-butylamine dihydrochloride.

1H-NMR(DMSO-D6, 200 MHz), •1.59(m,4H), 1.73(m,4H), 2.02(m,2H), 2.53(m,1H), 3.01(m,4H), 3.23(m,2H), 3.38(m,1H), 4.25(m,1H), 7.39(m,3H), 7.55(m,2H), 8.81(br,3H), 10.67(br,1H)

Example 50

1-Phenyl-5-(1-hexamethyleneimino)-n-pentylamine

The procedure given in Example 2 except for the formation of salts was followed using 5-bromo-1-(tert-butoxycarbonyl)amino-1-phenyl pentane as a reactant, instead of d-1-bromo-2-(tert-butoxycarbonyl)amino-3-phenyl propane to give 1-Phenyl-5-(1-hexamethyleneimino)-n-pentylamine.

1H-NMR(CDCl₃, 200 MHz), •1.28(m,2H), 1.45(m,2H), 1.52(m,12H), 2.42(t,2H), 2.58(m,4H), 3.89(t,1H), 7.29(m,5H)

Example 51

1-Phenyl-3-[1-(3-methylpiperidinyl)]-n-propylamine

The procedure given in Example 2 except for the formation of salts was followed using 3-bromo-1-(tert-butoxycarbonyl)amino-1-phenyl propane and 3-methylpiperidine as reactants, instead of d-1-bromo-2-(tert-butoxycarbonyl)amino-3-phenyl propane and hexamethyleneimine to give 1-Phenyl-3-[1-(3-methylpiperidinyl)]-n-propylamine.

1H-NMR(CDCl₃, 200 MHz), •0.82(d,4H), 1.42(s,1H), 1.64(m,4H), 1.76(m,3H), 1.89(q,2H), 2.31(m,2H), 2.84(m,2H), 3.99(t,1H), 7.28(t,5H)

Example 52

1-Phenyl-3-[1-(4-benzoylpiperidinyl)]-n-propylamine dihydrochloride

The procedure given in Example 2 was followed using 3-bromo-1-(tert-butoxycarbonyl)amino-1-phenyl propane and 4-benzoylpiperidine as reactants, instead of d-1-bromo-2-(tert-butoxycarbonyl)amino-3-phenyl propane and hexamethyleneimine to give 1-Phenyl-3-[1-(4-benzoylpiperidinyl)]-n-propylamine dihydrochloride.

1H-NMR(DMSO-D6, 200 MHz), •1.83(m,2H), 2.04(m, 4H), 2.15(s,1H), 3.23(m,3H), 3.69(m,3H), 4.05(m,1H), 7.53 (d,3H), 7.64(m,5H), 8.08(d,2H), 8.83(br,3H), 10.78(br,1H)

Example 53

1-Phenyl-3-[1-(1,2,3,4-tetrahydroisoquinolinyl)]-n-propylamine

The procedure given in Example 2 except for the formation of salts was followed using 3-bromo-1-(tert-butoxycarbonyl)amino-1-phenyl propane and 1,2,3,4-tetrahydroisoquinoline as reactants, instead of d-1-bromo-2-(tert-butoxycarbonyl)amino-3-phenyl propane and hexamethyleneimine to give 1-Phenyl-3-[1-(1,2,3,4-tetrahydroisoquinolinyl)]-n-propylamine.

1H-NMR(CDCl$_3$, 200 MHz), •1.99(t,2H), 2.04(t,2H), 2.56(q,2H), 2.73(d,2H), 2.91(t,2H), 3.59(s,2H), 4.09(q,1H), 7.02(t,1H), 7.08(d,3H), 7.28(d,1H), 7.33(d,3H)

Example 54

1-Phenyl-3-[1-(4-(4-fluorobenzoyl)piperidinyl)]-n-propylamine

The procedure given in Example 2 except for the formation of salts was followed using 3-bromo-1-(tert-butoxycarbonyl)amino-1-phenyl propane and 4-(4-fluorobenzoyl)piperidine as reactants, instead of d-1-bromo-2-(tert-butoxycarbonyl)amino-3-phenyl propane and hexamethyleneimine to give 1-Phenyl-3-[1-(4-(4-fluorobenzoyl)piperidinyl)]-n-propylamine.

1H-NMR(CDCl$_3$, 200 MHz), •1.89(m,5H), 1.99(m,2H), 2.32(m,2H), 2.98(m,6H), 3.98(m,1H), 7.09(q,2H), 7.28(m, 5H), 7.90(d,2H)

Example 55

1-Phenyl-3-[1-(4-(phenylacetyl)piperidinyl)]-n-propylamine

The procedure given in Example 2 except for the formation of salts was followed using 3-bromo-1-(tert-butoxycarbonyl)amino-1-phenyl propane and 4-(phenylacetyl)piperidine as reactants, instead of d-1-bromo-2-(tert-butoxycarbonyl)amino-3-phenyl propane and hexamethyleneimine to give 1-Phenyl-3-[1-(4-(phenylacetyl) piperidinyl)]-n-propylamine.

1H-NMR(CDCl$_3$, 200 MHz), •1.77(m,9H), 2.35(m,4H), 2.91(m,2H), 3.70(s,2H), 3.98(m,1H), 7.18(t,4H), 7.25(t,6H)

Example 56

[1-(3-Amino-3-phenyl-propyl)-piperidin-4-yl]-phenyl-methanol

The procedure given in Example 2 except for the formation of salts was followed using 3-bromo-1-(tert-butoxycarbonyl)amino-1-phenyl propane and phenyl-piperidin-4-yl-methanol as reactants, instead of d-1-bromo-2-(tert-butoxycarbonyl)amino-3-phenyl propane and hexamethyleneimine to give [1-(3-Amino-3-phenyl-propyl)-piperidin-4-yl]-phenyl-methanol.

1H-NMR(CDCl$_3$, 200 MHz), •1.59(m,2H), 1.85(q,4H), 2.02(d,2H), 2.31(m,3H), 2.43(br,2H), 2.83(d,1H), 2.97(d, 1H), 3.68(s,1H), 3.91(t,1H), 4.32(d,1H), 7.31(br,10H)

Example 57

[1-(3-Amino-3-phenyl-propyl)-piperidin-4-yl]-(4-fluoro-phenyl)-methanol

The procedure given in Example 2 was followed using 3-bromo-1-(tert-butoxycarbonyl)amino-1-phenyl propane and (4-fluorophenyl)-piperidin-4-yl-methanol as reactants, instead of d-1-bromo-2-(tert-butoxycarbonyl)amino-3-phenyl propane and hexamethyleneimine to give [1-(3-Amino-3-phenyl-propyl)-piperidin-4-yl]-(4-fluoro-phenyl)-methanol.

1H-NMR(CDCl$_3$, 200 MHz), •1.41(m,3H), 1.75(br,3H), 1.88(d,2H), 2.21(m,2H), 2.75(m,3H), 2.82(m,2H), 3.55(m, 1H), 3.83(br,1H), 4.23(d,1H), 6.98(t,2H), 7.25(br,7H)

Example 58

N-Benzoyl-1-(3,4-dichlorobenzyl)-2-(1-hexamethyleneimino)ethylamine

To a solution of 1-(3,4-dichlorobenzyl)-2-(1-hexamethyleneimino)ethylamine dihydrochloride (1 mmol) and triethylamine (3.5 equiv) in dichloromethane, benzoylchloride (1.2 equiv) was slowly added at 0°. After 0.5 h, the reaction mixture was evaporated under vaccum and ethyl acetate was poured to form a white precipitate. The solution was filtered and the filtrate was washed 2N NaOH and saturated NaCl, dried (MgSO4) and concentrated in vacuo. The residue was purified by column chromatography, eluting with an increasing ratio of ethyl acetate in hexane to afford N-benzoyl-1-(3,4-dichlorobenzyl)-2-(1-hexamethyleneimino)ethylamine; Yield 70%

1H-NMR(CDCl$_3$, 200 MHz), •1.52(s,8H), 2.65(s,6H), 3.21(t,2H), 4.34(q,1H), 6.74(d,1H), 7.19(m,1H), 7.27(d, 1H), 7.46(m,4H), 7.76(d,2H)

Example 59 d-N-(2-Nitrobenzenesulfonyl)-1-benzyl-2-(1-pyrrolidinyl)ethylamine hydrochloride The procedure given in Example 58 was followed using d-1-benzyl-2-(1-pyrrolidinyl)ethylamine and 2-nitrobenzenesulfonyl chloride as reactants, instead of 1-(3,4-dichlorobenzyl)-2-(1-hexamethyleneimino)ethylamine dihydrochloride and benzoylchloride to give d-N-(2-nitrobenzenesulfonyl)-1-benzyl-2-(1-pyrrolidinyl) ethylamine hydrochloride. The resulting product was dissolved in 6% HCl-MeOH solution and allowed to stir for 2 h. The solvent was removed under reduced pressure and tritulated with THF to afford d-N-(2-Nitrobenzenesulfonyl)-1-benzyl-2-(1-pyrrolidinyl)ethylamine hydrochloride.

1H-NMR(DMSO-D6, 200 MHz), •1.98(m,4H), 3.08(m, 3H), 3.40(m,2H), 3.12(m,3H), 3.92(m,1H), 6.98(d,3H), 7.06 (s,2H), 7.68(m,2H), 7.77(t,1H), 7.84(t,1H), 8.42(d,1H), 10.08(br,1H)

Example 60

N-Methyl-N-[2-(3,4-Dichlorophenyl)acetyl]-1-[4-(tert-butyl) benzyl]-2-(1-hexamethyleneimino)ethylamine The procedure given in Example 58 was followed using N-methyl-1-[4-(tert-butyl)benzyl]-2-(1-hexamethyleneimino)ethylamine and 2-(3,4-Dichlorophenyl)acetyl chloride as reactants, instead of 1-(3,4-dichlorobenzyl)-2-(1-hexamethyleneimino)ethylamine dihydrochloride and benzoylchloride to give N-methyl-N-[2-(3,4-Dichlorophenyl)acetyl]-1-[4-(tert-butyl)benzyl]-2-(1-hexamethyleneimino)ethylamine.

1H-NMR(CDCl$_3$, 200 MHz), •1.23(s,9H), 1.53(d,8H), 2.57(m,7H), 2.73(s,2H), 2.85(s,3H), 3.02(q,1H), 3.52(s,$_1$H), 6.78(dd,1H), 7.01(d,1H), 7.09(d,1H), 7.25(m,4H)

Example 61

N-Benzoyl-1-(3,4-dichlorobenzyl)-2-[1-(4-benzylpiperidinyl)]ethylamine

The procedure given in Example 58 was followed using 1-(3,4-dichlorobenzyl)-2-[1-(4-benzylpiperidinyl)]ethylamine as a reactant, instead of 1-(3,4-dichlorobenzyl)-2-(1-hexamethyleneimino)ethylamine dihydrochloride to give N-benzoyl-1-(3,4-dichlorobenzyl)-2-[1-(4-benzylpiperidinyl)]ethylamine.

1H-NMR(CDCl$_3$, 200 MHz), •1.28(t,2H), 1.60(m,2H), 1.91(m,2H), 2.05(t,2H), 2.49(m,3H), 2.88(m,2H), 3.17(d, 2H), 4.43(m,1H), 6.68(m,1H)7.12(m,3H), 7.23(m,4H), 7.39(d,2H), 7.48(m,2H), 7.73(d,2H)

Example 62

N-[2-(3,4-Dichlorophenyl)acetyl]-1-(3,4-dichlorobenzyl)-2-[1-(4-benzylpiperidinyl)]ethylamine The procedure given in Example 58 was followed using 1-(3,4-dichlorobenzyl)-2-[1-(4-benzylpiperidinyl)]ethylamine and 2-(3,4-dichlorophenyl)acetyl chloride as reactants, instead of 1-(3,4-dichlorobenzyl)-2-(1-hexamethyleneimino)ethylamine dihydrochloride and benzoylchloride to give N-[2-(3,4-Dichlorophenyl)acetyl]-1-(3,4-dichlorobenzyl)-2-[1-(4-benzyl piperidinyl)]ethylamine.

1H-NMR(CDCl$_3$, 200 MHz), •1.26(s,2H), 1.44(s,$_1$H), 1.58(m,2H), 1.84(t,$_1$H), 2.09(m,1H), 2.32(m,1H), 2.51(d, 3H), 2.75(m,2H), 2.97(t,2H), 3.45(s,2H), 4.21(m,1H), 6.14(br,1H), 7.08(m,6H), 7.26(m,2H), 7.31(m,3H)

Example 63

N-[2-(3,4-Dichlorophenyl)acetyl]-1-(3,4-dichlorobenzyl)-2-(1-hexamethyleneimino)ethylamine The procedure given in Example 58 was followed using 2-(3,4-dichlorophenyl)acetyl chloride as a reactant, instead of benzoylchloride to give N-[2-(3,4-dichlorophenyl)acetyl]-1-(3,4-dichlorobenzyl)-2-(1-hexamethyleneimino) ethylamine.

1H-NMR(CDCl$_3$, 200 MHz), •1.49(s,8H), 2.61(m,6H), 2.99(d,2H), 3.42(s,2H), 4.18(q,1H), 6.04(br,1H), 7.06(d, 1H), 7.12(s,2H), 7.34(m,3H)

Example 64

N-Benzoyl-1-(2,4-dichlorobenzyl)-2-[1-(4-benzylpiperidinyl)]ethylamine

The procedure given in Example 58 was followed using 1-(2,4-dichlorobenzyl)-2-[1-(4-benzylpiperidinyl)]ethylamine as a reactant, instead of 1-(3,4-dichlorobenzyl)-2-(1-hexamethyleneimino)ethylamine dihydrochloride to give N-benzoyl-1-(2,4-dichlorobenzyl)-2-[1-(4-benzylpiperidinyl)]ethylamine.

1H-NMR(CDCl$_3$, 200 MHz), •1.61(t,4H), 1.91(t,1H), 2.09(t,1H), 2.52(m,4H), 2.89(m,2H), 3.17(d,2H), 4.41(q, 1H), 6.69(m,1H), 7.16(q,3H), 7.23(t,4H), 7.38(s,1H), 7.48(t,3H), 7.75(d,2H)

Example 65

N-[2-(3,4-Dichlorophenyl)acetyl]-1-(2,4-dichlorobenzyl)-2-[1-(4-benzylpiperidinyl)]ethylamine The procedure given in Example 58 was followed using 1-(2,4-dichlorobenzyl)-2-[1-(4-benzylpiperidinyl)]ethylamine and 2-(3,4-dichlorophenyl)acetyl chloride as reactants, instead of 1-(3,4-dichlorobenzyl)-2-(1-hexamethyleneimino)ethylamine dihydrochloride and benzoylchloride to give N-[2-(3,4-Dichlorophenyl)acetyl]-1-(2,4-dichlorobenzyl)-2-[1-(4-benzyl piperidinyl)]ethylamine.

1H-NMR(CDCl$_3$, 200 MHz), •1.58(m,6H), 2.01(m,1H), 2.31(m,2H), 2.50(d,2H), 2.74(m,2H), 2.97(m,2H), 3.41(s, 2H), 4.21(m,1H), 6.05(m,1H), 7.12(m,4H), 7.25(m,7H)

Example 66

N-[2-(3,4-Dichlorophenyl)acetyl]-1-phenyl-3-(1-hexamethyleneimino)-n-propylamine The procedure given in Example 58 was followed using 1-phenyl-3-(1-hexamethyleneimino)-n-propylamine and 2-(3,4-dichloro phenyl)acetyl chloride as reactants, instead of 1-(3,4-dichlorobenzyl)-2-(1-hexamethyleneimino)ethylamine dihydrochloride and benzoylchloride to give N-[2-(3,4-dichlorophenyl)acetyl]-1-phenyl-3-(1-hexamethyleneimino)-n-propylamine.

1H-NMR(CDCl$_3$, 200 MHz), •1.59(s,8H), 1.69(m,1H), 2.04(m,1H), 2.39(m,2H), 2.54(d,4H), 3.46(s,2H), 5.12(q, 1H), 7.15(m,3H), 7.26(m,3H), 7.40(m,2H), 8.74(d,1H)

Example 67

N-(p-Toluenesulfonyl)-1-phenyl-3-(1-hexamethyleneimino)-n-propylamine

The procedure given in Example 58 was followed using 1-phenyl-3-(1-hexamethyleneimino)-n-propylamine and p-toluenesulfonyl chloride as reactants, instead of 1-(3,4-dichlorobenzyl)-2-(1-hexamethyleneimino)ethylamine dihydrochloride and benzoylchloride to give N-(p-toluenesulfonyl)-1-phenyl-3-(1-hexamethyleneimino)-n-propylamine.

1H-NMR(CDCl$_3$, 200 MHz), •1.69(m,8H), 2.26(m,1H), 2.36(s,3H), 2.49(m,3H), 2.59(d,4H), 4.51(m,1H), 7.13(m, 7H), 7.22(m,1H), 7.54(d,2H)

Example 68

N-Benzoyl-1-phenyl-3-(1-hexamethyleneimino)-n-propylamine

The procedure given in Example 58 was followed using 1-phenyl-3-(1-hexamethyleneimino)-n-propylamine as a reactant, instead of 1-(3,4-dichlorobenzyl)-2-(1-hexamethyleneimino)ethylamine dihydrochloride to give N-benzoyl-1-phenyl-3-(1-hexamethyleneimino)-n-propylamine.

1H-NMR(CDCl$_3$, 200 MHz), •1.53(m,4H), 1.69(m,4H), 2.14(m,1H), 2.52(m,2H), 2.64(m,4H), 5.27(m,2H), 7.24(s, 5H), 7.46(m,3H), 7.85(d, 2H), 9.44(s,1H)

Example 69

N-[2-(3,4-Dichlorophenyl)acetyl]-1-phenyl-3-[1-(4-benzylpiperidinyl)]-n-propylamine The procedure given in Example 58 was followed using 1-phenyl-3-[1-(4-benzylpiperidinyl)]-n-propylamine and 2-(3,4-dichlorophenyl)acetyl chloride as reactants, instead of 1-(3,4-dichlorobenzyl)-2-(1-hexamethyleneimino)ethylamine dihydrochloride and benzoylchloride to give N-[2-(3,4-dichlorophenyl)acetyl]-1-phenyl-3-[1-(4-benzylpiperidinyl)]-n-propylamine.

1H-NMR(CDCl$_3$, 200 MHz), •1.75(m,4H), 1.85(t,3H), 2.08(m,2H), 2.32(m,2H), 2.59(d,2H), 2.82(d,1H), 3.03(d, 1H), 3.48(s,2H), 5.11(q,1H), 7.19(t,5H), 7.28(d,6H), 7.41(t, 2H), 8.52(d,1H)

Example 70

N-[2-(3,4-Dichlorophenyl)acetyl]-1-phenyl-3-(1-(4-fluorobenzoylpiperidinyl))-n-propylamine The procedure given in Example 58 was followed using 1-phenyl-3-(1-(4-fluorobenzoylpiperidinyl))-n-propylamine and 2-(3,4-dichlorophenyl)acetyl chloride as reactants, instead of 1-(3,4-dichlorobenzyl)-2-(1-hexamethyleneimino)ethylamine dihydrochloride and benzoylchloride to give N-[2-(3,4-dichlorophenyl)acetyl]-1-phenyl-3-(1-(4-fluorobenzoyl piperidinyl))-n-propylamine.

1H-NMR(CDCl$_3$, 200 MHz), •1.91(m,4H), 2.08(m,2H), 2.23(m,2H), 2.33(m,2H), 2.89(d,1H), 3.04(d,1H), 3.23(m, 1H), 3.56(s,2H), 5.13(q,1H), 7.21(m,10H), 7.99(m,2H), 8.28(d,1H)

Example 71

N-(p-Toluenesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and p-toluenesulfonyl chloride as reactants, instead of 1-(3,4-dichlorobenzyl)-2-(1-hexamethyleneimino)ethylamine dihydrochloride and benzoylchloride to give N-(p-toluenesulfonyl)-1-phenyl-3-[1-(4-benzylpiperidinyl)]-n-propylamine.

1H-NMR(CDCl$_3$, 200 MHz), •1.51(m,3H), 1.76(m,5H), 2.36(m,5H), 2.61(d,2H), 2.96(m,3H), 4.48(m,1H), 7.17(m, 13H), 7.68(d,2H)

Example 72

N-(Benzenesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and benzenesulfonyl chloride as reactants, instead of 1-(3,4-dichlorobenzyl)-2-(1-hexamethyleneimino)ethylamine dihydrochloride and benzoylchloride to give N-(benzenesulfonyl)-1-phenyl-3-[1-(4-benzylpiperidinyl)]-n-propylamine.

1H-NMR(CDCl$_3$, 200 MHz), •1.50(m,4H), 1.75(m,4H), 1.89(d,2H), 2.34(q,2H), 2.61(d,2H), 2.90(m,2H), 4.53(t, 1H), 7.11(s,6H), 7.36(m,7H), 7.70(d,2H)

Example 73

N-(2,4-Dinitrobenzenesulfonyl)-1-phenyl-3-[1-(4-benzylpiperidinyl)]-n-propylamine The procedure given in Example 58 was followed using 1-phenyl-3-[1-(4-benzylpiperidinyl)]-n-propylamine and 2,4-dinitrobenzenesulfonyl chloride as reactants, instead of 1-(3,4-dichlorobenzyl)-2-(1-hexamethyleneimino)ethylamine dihydrochloride and benzoylchloride to give N-(2, 4-dinitrobenzenesulfonyl)-1-phenyl-3-[1-(4-benzylpiperidinyl)]-n-propylamine.

1H-NMR(CDCl$_3$, 200 MHz), •1.98(m,2H), 2.22(m,2H), 2.49(m,4H), 2.68(m,3H), 3.01(m,2H), 3.22(m,2H), 4.92(q, 1H), 7.03(d,5H), 7.22(t,6H), 7.49(d,1H), 7.95(d,1H), 8.46 (s,1H)

Example 74

N-(Methanesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and methanesulfonyl chloride as reactants, instead of 1-(3,4-dichlorobenzyl)-2-(1-hexamethyleneimino)ethylamine dihydrochloride and benzoylchloride to give N-(methanesulfonyl)-1-phenyl-3-[1-(4 benzylpiperidinyl)]-n-propylamine.

1H-NMR(CDCl$_3$, 200 MHz), •1.38(m,2H), 1.50(m,2H), 1.71(d,2H), 1.91(m,4H), 2.50(s,3H), 2.59(m,4H), 3.05(t, 2H), 4.69(t,1H), 7.17(t,2H), 7.27(q,4H), 7.36(d,4H)

Example 75

N-(3-Nitrobenzenesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and 3-nitrobenzenesulfonyl chloride as reactants, instead of 1-(3, 4-dichlorobenzyl)-2-(1-hexamethyleneimino)ethylamine dihydrochloride and benzoylchloride to give N-(3-nitrobenzenesulfonyl)-1-phenyl-3-[1-(4-benzylpiperidinyl)]-n-propylamine.

1H-NMR(CDCl$_3$, 200 MHz), •1.45(t,2H), 1.59(d,2H), 1.81(m,3H), 2.01(m,2H), 2.51(t,2H), 2.63(d,2H), 3.7(d,2H), 4.65(t,1H), 7.04(s,5H), 7.23(s,1H), 7.26(q,5H), 7.46(t,1H), 7.89(d,1H), 8.21(d,1H), 8.31(s,1H)

Example 76

N-(2-Nitrobenzenesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and 2-nitrobenzenesulfonyl chloride as reactants, instead of 1-(3,4-dichlorobenzyl)-2-(1-hexamethyleneimino)ethylamine dihydrochloride and benzoylchloride to give N-(2-nitrobenzenesulfonyl)-1-phenyl-3-[1-(4-benzylpiperidinyl)]-n-propylamine.

1H-NMR(CDCl$_3$, 200 MHz), •1.98(m,2H), 2.22(m,2H), 2.49(m,4H), 2.68(m,3H), 3.01(m,2H), 3.22(m,2H), 4.92(q,1H), 7.01(m,3H), 7.21(d,3H), 7.25(s,6H), 7.43(m,2H), 7.69(d,1H)

Example 77

N-(2,4,6-Triisopropylbenzenesulfonyl)-1-phenyl-3-[1-(4-benzylpiperidinyl)]-n-propylamine The procedure given in Example 58 was followed using 1-phenyl-3-[1-(4-benzylpiperidinyl)]-n-propylamine and 2,4,6-triisopropylbenzenesulfonyl chloride as reactants, instead of 1-(3,4-dichlorobenzyl)-2-(1-hexamethyleneimino)ethylamine dihydrochloride and benzoylchloride to give N-(2,4,6-triisopropylbenzenesulfonyl)-1-phenyl-3-[1-(4-benzylpiperidinyl)]-n-propylamine.

1H-NMR(CDCl$_3$, 200 MHz), •1.08(d,6H), 1.25(t,12H), 1.45(m,1H), 1.54(m,2H), 1.74(d,3H), 1.89(m,4H), 2.48(m,2H), 2.59(d,2H), 2.86(m,1H), 2.99(d,1H), 3.12(d,1H), 4.03(m,2H), 4.80(m,1H), 7.02(d,7H), 7.19(d,2H), 7.28(t,3H)

Example 78

N-Benzoyl-1-phenyl-3-[1-(4-benzylpiperidinyl)]-n-propylamine

The procedure given in Example 58 was followed using 1-phenyl-3-[1-(4-benzylpiperidinyl)]-n-propylamine as a reactant, instead of 1-(3,4-dichlorobenzyl)-2-(1-hexamethyleneimino)ethylamine dihydrochloride to give N-benzoyl-1-phenyl-3-[1-(4-benzylpiperidinyl)]-n-propylamine.

1H-NMR(CDCl$_3$, 200 MHz), •1.64(m,7H), 1.89(d,1H), 1.97(t,1H), 2.29(m,2H), 2.55(d,2H), 2.95(d,1H), 3.08(d,1H), 5.35(q,1H), 7.13(d,2H), 7.30(q,8H), 7.49(q,3H), 7.96(d,2), 9.55(d,1H)

Example 79

N-(2-Thiophenesulfonyl)-1-phenyl-3-[1-(4-benzylpiperidinyl)]-n-propylamine

The procedure given in Example 58 was followed using 1-phenyl-3-[1-(4-benzylpiperidinyl)]-n-propylamine and 2-thiophenesulfonyl chloride as reactants, instead of 1-(3,4-dichlorobenzyl)-2-(1-hexamethyleneimino)ethylamine dihydrochloride and benzoylchloride to give N-(2-thiophenesulfonyl)-1-phenyl-3-[1-(4-benzylpiperidinyl)]-n-propylamine.

1H-NMR(CDCl$_3$, 200 MHz), •1.44(m,2H), 1.51(d,2H), 1.73(d,3H), 1.87(m,3H), 2.37(m,2H), 2.59(d,2H), 2.95(d,2H), 4.59(m,1H), 6.94(t,1H), 7.21(m,1OH), 7.39(d,1H), 7.48(d,1H)

Example 80

N-(2-Nitrobenzenesulfonyl)-1-phenyl-3-[1-(4-benzoylpiperidinyl)]-n-propylamine

The procedure given in Example 58 was followed using 1-phenyl-3-[1-(4-benzoylpiperidinyl)]-n-propylamine and 2-nitrobenzenesulfonyl chloride as reactants, instead of 1-(3,4-dichlorobenzyl)-2-(1-hexamethyleneimino)ethylamine dihydrochloride and benzoylchloride to give N-(2-nitrobenzenesulfonyl)-1-phenyl-3-[1-(4-benzoylpiperidinyl)]-n-propylamine.

1H-NMR(CDCl$_3$, 200 MHz), •2.01(m,4H), 2.22(m,2H), 2.42(m,1H), 2.99(dd,1H), 3.38(m,1H), 3.57(m,1H), 4.34(d,2H), 4.69(m,1H), 4.88(m,1H), 7.05(s,4H), 7.25(s,2H), 7.32(d,3H), 7.46(t,3H), 7.67(d,1H), 7.95(d,2H)

Example 81

N-(2-Nitrobenzenesulfonyl)-1-phenyl-3-[1-(4-(4-fluorobenzoyl) piperidinyl)]-n-propylamine The procedure given in Example 58 was followed using 1-phenyl-3-[1-(4-(4-fluorobenzoyl)piperidinyl)]-n-propylamine and 2-nitrobenzenesulfonyl as reactants, instead of 1-(3,4-dichlorobenzyl)-2-(1-hexamethyleneimino)ethylamine dihydrochloride and benzoylchloride to give N-(2-nitrobenzenesulfonyl)-1-phenyl-3-[1-(4-(4-fluorobenzoyl) piperidinyl)]-n-propylamine.

1H-NMR(CDCl$_3$, 200 MHz), •1.82(m,1H), 2.01(m,3H), 2.21(m,4H), 2.39(m,2H), 2.89(d,1H), 3.05(d,1H), 3.29(m,1H), 3.64(s,1H), 4.87(t,1H), 7.05(m,4H), 7.15(t,3H), 7.26(d,1H), 7.41(d,2H), 7.63(d,1H), 7.99(t,2H)

Example 82

N-(2-Thiophenesulfonyl)-1-phenyl-3-[1-(1,2,3,4-tetrahydroisoquinolinyl)]-n-propylamine The procedure given in Example 58 was followed using 1-phenyl-3-[1-(1,2,3,4-tetrahydroisoquinolinyl)]-n-propylamine and 2-thiophenesulfonyl chloride as reactants, instead of 1-(3,4-dichlorobenzyl)-2-(1-hexamethyleneimino)ethylamine dihydrochloride and benzoylchloride to give N-(2-thiophenesulfonyl)-1-phenyl-3-[1-(1,2,3,4-tetrahydroisoquinolinyl)]-n-propylamine.

1H-NMR(CDCl$_3$, 200 MHz), •1.91(m,1H), 2.01(m,1H), 2.06(m,1H), 2.53(m,1H), 2.61(m,1H), 2.68(m,1H), 2.89(t,1H), 2.97(d,1H), 3.03(m,1H), 3.60(q,2H), 4.69(t,1H), 6.91(q,1H), 7.04(m,1H), 7.16(d,3H), 7.22(d,5H), 7.32(s,1H), 7.45(d,1H)

Example 83

N-Benzoyl-1-phenyl-3-[1-(4-benzoylpiperidinyl)]-n-propylamine

The procedure given in Example 58 was followed using 1-phenyl-3-[1-(4-benzoylpiperidinyl)]-n-propylamine as a reactant, instead of 1-(3,4-dichlorobenzyl)-2-(1-hexamethyleneimino)ethylamine dihydrochloride to give N-benzoyl-1-phenyl-3-[1-(4-benzoylpiperidinyl)]-n-propylamine.

1H-NMR(CDCl$_3$, 200 MHz), •1.99(m,4H), 2.23(m,2H), 2.51(dd,1H), 3.14(dd,1H), 3.41(m,1H), 3.55(m,1H), 4.29(t,2H), 4.67(t,1H), 5.78(br,1H), 7.32(m,1OH), 7.51(m,3H), 7.96(d,2H), 9.29(m,1H)

Example 84

N-[2-(3,4-Dichlorophenyl)acetyl]-1-phenyl-3-[1-(4-benzoylpiperidinyl)]-n-propylamine The procedure given in Example 58 was followed using 1-phenyl-3-[1-(4-benzoylpiperidinyl)]-n-propylamine and 2-(3,4-dichlorophenyl)acetyl chloride as reactants, instead of 1-(3,4-dichlorobenzyl)-2-(1-hexamethyleneimino)ethylamine dihydrochloride and benzoylchloride to give N-[2-(3,4-Dichlorophenyl)acetyl]-1-phenyl-3-[1-(4-benzoylpiperidinyl)]-n-propylamine.

1H-NMR(CDCl$_3$, 200 MHz), •1.85(m,5H), 2.11(m,3H), 2.39(m,2H), 2.91(d,1H), 3.09(d,1H), 3.33(m,1H), 3.49(s,2H), 5.12(q,1H), 7.19(m,7H), 7.46(m,4H), 7.96(d,2H), 8.29(m,1H)

Example 85

N-Benzenesulfonyl-1-phenyl-3-[1-(4-benzoylpiperidinyl)]-n-propylamine

The procedure given in Example 58 was followed using 1-phenyl-3-[1-(4-benzoylpiperidinyl)]-n-propylamine and benzenesulfonyl chloride as reactants, instead of 1-(3,4-dichlorobenzyl)-2-(1-hexamethyleneimino)ethylamine dihydrochloride and benzoylchloride to give N-benzenesulfonyl-1-phenyl-3-[1-(4-benzoylpiperidinyl)]-n-propylamine.

1H-NMR(CDCl$_3$, 200 MHz), •1.80(m,3H), 1.91(m,4H), 2.13(t,1H), 2.13(d,1H), 2.38(m,2H), 2.95(d,2H), 3.27(q,1H), 4.59(m,1H), 7.10(s,5H), 7.40(m,6H), 7.68(d,2H), 7.92(d,2H)

Example 86

N-Acetyl-1-phenyl-3-[1-(4-benzylpiperidinyl)]-n-propylamine

The procedure given in Example 58 was followed using 1-phenyl-3-[1-(4-benzylpiperidinyl)]-n-propylamine and acetyl chloride as reactants, instead of 1-(3,4-dichlorobenzyl)-2-(1-hexamethyleneimino)ethylamine dihydrochloride and benzoylchloride to give N-acetyl-1-phenyl-3-[1-(4-benzylpiperidinyl)]-n-propylamine.

1H-NMR(CDCl$_3$, 200 MHz), •1.75(m,3H), 1.91(d,2H), 2.00(s,3H), 2.08(s,2H), 2.19(m,2H), 2.32(m,2H), 2.59(d,2H), 2.87(d,1H), 3.08(d,1H), 5.10(q,1H), 7.17(t,4H), 7.26(m,6H), 8.39(d,1H)

Example 87

N-Benzyl-1-(3,4-dichlorobenzyl)-2-(1-hexamethyleneimino)ethylamine

To a stirred solution of freshly prepared 1 M alane (5mmol) was added dropwise over 15 min a solution of N-benzoyl-1-(3,4-dichlorobenzyl)-2-(1-hexamethyleneimino)ethylamine (1mmol). In order to prevent the reaction mixture from heating to the point of reflux of the THF, it was periodically immersed in an ice bath to keep the temperature around room temperature. 30 min after addition of reagent was complete, the reaction mixture was carefully poured into a large beaker containing 30 mL of 15% aqueous NaOH, and the mixture was vigorously stirred during the addition. After the quenching was complete, the aqueous mixture was cooled to room temperature and enough chloroform was added to result in a lower organic layer. The organic extract was separated, dried (MgSO$_4$) and concentrated in vacuo. to give the crude product as a pale yellow oil. The oil was purified by column chromatography, eluting with an increasing ratio of methanol in ethyl acetate to afford N-benzyl-1-(3,4-dichlorobenzyl)-2-(1-hexamethyleneimino)ethylamine: Yield 45%

1H-NMR(CDCl$_3$, 200 MHz), •1.51(s,8H), 2.49(m,6H), 2.62(m,2H), 2.99(m,2H), 3.81(q,2H), 7.29(m,8H)

Example 88

N-Benzyl-1-[4-(tert-butyl)benzyl]-2-(1-hexamethyleneimino)ethylamine

The procedure given in Example 87 was followed using N-benzoyl-1-[4-(tert-butyl)benzyl]-2-(1-hexamethyleneimino)ethylamine as a reactant, instead of N-benzoyl-1-(3,4-dichlorobenzyl)-2-(1-hexamethyleneimino)ethylamine to give N-benzyl-1-[4-(tert-butyl)benzyl]-2-(1-hexamethyleneimino)ethylamine.

1H-NMR(CDCl$_3$, 200 MHz), •0.90(m,1H), 1.30(s,9H), 1.52(s,8H), 2.50(m,7H), 2.82(m,2H), 3.75(q,2H), 7.13(m,2H), 7.28(m,7H)

Example 89

N-Benzyl-1-(3,4-dichlorobenzyl)-2-[1-(4-benzylpiperidinyl)]ethylamine

The procedure given in Example 87 was followed using N-benzoyl-1-(3,4-dichlorobenzyl)-2-[1-(4-benzylpiperidinyl)]ethylamine as a reactant, instead of N-benzoyl-1-(3,4-dichlorobenzyl)-2-(1-hexamethyleneimino)ethylamine to give N-benzyl-1-(3,4-dichlorobenzyl)-2-[1-(4-benzylpiperidinyl)]ethylamine.

1H-NMR(CDCl$_3$, 200 MHz), •1.65(m,4H), 1.98(m,6H), 2.51(d,3H), 2.69(t,2H), 2.98(m,2H), 3.82(q,2H), 7.12(t,5H), 7.28(m,7H), 7.36(s,1H)

Example 90

N-(3,4-Dichlorophenethyl-1-(3,4-dichlorobenzyl)-2-(1-hexamethyleneimino)ethylamine The procedure given in Example 87 was followed using N-(3,4-dichlorophenyl)acetyl-1-(3,4-dichlorobenzyl)-2-(1-hexamethyleneimino)ethylamine as a reactant, instead of N-benzoyl-1-(3,4-dichlorobenzyl)-2-(1-hexamethyleneimino)ethylamine to give N-(3,4-dichlorophenethyl-1-(3,4-dichlorobenzyl)-2-(1-hexamethyleneimino)ethylamine.

1H-NMR(CDCl$_3$, 200 MHz), •1.38(s,8H), 2.11(m,2H), 2.41(m,6H), 2.64(m,1H), 2.75(m,3H), 3.01(m,2H), 7.12(m,2H), 7.14(s,1H), 7.37(d,3H)

Example 91

N-(3,4-Dichlorophenethyl)-1-phenyl-3-(1-hexamethyleneimino)-n-propylamine

The procedure given in Example 87 was followed using N-(3,4-dichlorophenyl)acetyl-1-phenyl-3-(1-hexamethyleneimino)-n-propylamine as a reactant, instead of N-benzoyl-1-(3,4-dichlorobenzyl)-2-(1-hexamethyleneimino)ethylamine to give N-(3,4-dichlorophenethyl)-1-phenyl-3-(1-hexamethyleneimino)-n-propylamine.

1H-NMR(CDCl$_3$, 200 MHz), •0.91(m,1H), 1.54(s,8H), 2.19(m,2H), 2.41(m,2H), 2.55(m,4H), 2.69(m,3H), 3.69(m, 1H), 7.00(d,1H), 7.23(m,7H)

Example 92

N-(3,4-Dichlorophenethyl)-1-phenyl-3-[1-(4-benzylpiperidinyl)]-n-propylamine

The procedure given in Example 87 was followed using N-(3,4-dichlorophenyl)acetyl-1-phenyl-3-[1-(4-benzylpiperidinyl)]-n-propylamine as a reactant, instead of N-benzoyl-1-(3,4-dichlorobenzyl)-2-(1-hexamethyleneimino) ethylamine to give N-(3,4-Dichlorophenethyl)-1-phenyl-3-[1-(4-benzylpiperidinyl)]-n-propylamine.

1H-NMR(CDCl$_3$, 200 MHz), •1.28(t,3H), 1.59(d,2H), 1.87(m,4H), 2.31(m,4H), 2.51(d,2H), 2.61(s,3H), 2.88(t, 2H), 3.64(t,1H), 7.01(d,1H), 7.13(m,4H), 7.23(m,8H)

Example 93

N-Formyl-1-(3,4-dichlorobenzyl)-2-(1-hexamethyleneimino)ethylamine

A mixture of 1-(3,4-dichlorobenzyl)-2-(1-hexamethyleneimino)ethylamine (1 mmol) and ethyl formate (50 mL) was refluxed overnight under an N$_2$ atmosphere. Then the solvent was evaporated in vacuo, and the oily residue was distilled in vacuo to give N-formyl-1-(3,4-dichlorobenzyl)-2-(1-hexamethyleneimino)ethylamine ethylamine: Yield 97%

1H-NMR(CDCl$_3$, 200 MHz), •1.59(s,5H), 1.72(s,3H), 2.69(m,2H), 2.81(m,2H), 2.89(m,2H), 3.06(d,2H), 4.46(m, 1H), 7.08(d,1H), 7.23(m,2H), 7.39(s,1H), 8.19(d,1H)

Example 94

N-Formyl-1-(3,4-dichlorobenzyl)-2-[1-(4-benzylpiperidinyl)]ethylamine

The procedure given in Example 93 was followed using 1-(3,4-dichlorobenzyl)-2-[1-(4-benzylpiperidinyl)]ethylamine as a reactant, instead of 1-(3,4-dichlorobenzyl)-2-(1-hexamethyleneimino)ethylamine to give N-Formyl-1-(3,4-dichlorobenzyl)-2-[1-(4-benzylpiperidinyl)]ethylamine.

1H-NMR(CDCl$_3$, 200 MHz), •1.30(m,2H), 1.57(m,3H), 1.74(m,2H), 2.03(m,1H), 2.41(m,2H), 2.49(d,2H), 2.81(d, 2H), 3.05(d,1H), 4.34(q,1H), 5.89(m,1H), 7.21(m,7H), 7.37 (s,1H), 8.13(s,1H)

Example 95

N-Formyl-1-[4-(tert-butyl)benzyl]-2-[1-(4-benzylpiperidinyl)]ethylamine

The procedure given in Example 93 was followed using 1-[4-(tert-butyl)benzyl]-2-[1-(4-benzylpiperidinyl)]ethylamine as a reactant, instead of 1-(3,4-dichlorobenzyl)-2-(1-hexamethyleneimino)ethylamine to give N-formyl-1-[4-(tert-butyl)benzyl]-2-[1-(4-benzylpiperidinyl)]ethylamine.

1H-NMR(CDCl$_3$, 200 MHz), •1.25(s,9H), 1.81(m,6H), 2.59(m,6H), 3.08(m,1H), 3.48(m,2H), 4.63(m,1H), 7.10(m, 5H), 7.31(m,4H), 8.27(s,1H), 8.62(d,1H)

Example 96

N-Formyl-1-(2,4-dichlorobenzyl)-2-[1-(4-benzylpiperidinyl)]ethylamine

The procedure given in Example 93 was followed using 1-(2,4-dichlorobenzyl)-2-[1-(4-benzylpiperidinyl)]ethylamine as a reactant, instead of 1-(3,4-dichlorobenzyl)-2-(1-hexamethyleneimino)ethylamine to give N-formyl-1-(2,4-dichlorobenzyl)-2-[1-(4-benzylpiperidinyl)]ethylamine.

1H-NMR(CDCl$_3$, 200 MHz), •1.27(m,2H), 1.62(d,4H), 2.06(m,1H), 2.39(t,1H), 2.49(d,3H), 2.89(d,2H), 3.03(d, 2H), 4.37(m,1H), 6.17(m,1H), 7.12(m,2H), 7.19(m,2H), 7.22(m,3H), 7.38(s,1H), 8.16(s,1H)

Example 97

N-Formyl-1-phenyl-3-[1-(4-benzylpiperidinyl)]-n-propylamine

The procedure given in Example 93 was followed using 1-phenyl-3-[1-(4-benzylpiperidinyl)]-n-propylamine as a reactant, instead of 1-(3,4-dichlorobenzyl)-2-(1-hexamethyleneimino)ethylamine to give N-formyl-1-phenyl-3-[1-(4-benzylpiperidinyl)]-n-propylamine.

1H-NMR(CDCl$_3$, 200 MHz), •1.81(m,8H), 2.11(m,1H), 2.29(m,2H), 2.57(d,2H), 2.84(d,1H), 3.08(d,3H), 5.25(m, 1H), 7.24(m,10H), 8.22(s,1H), 8.37(br,1H)

Example 98

N-(3,4-Dichlorophenethyl)-N-formyl-1-phenyl-3-[1-(4-benzylpiperidinyl)]-n-propylamine The procedure given in Example 93 was followed using N-(3,4-dichlorophenethyl)-1-phenyl-3-[1-(4-benzylpiperidinyl)]-n-propylamine as a reactant, instead of 1-(3,4-dichlorobenzyl)-2-(1-hexamethyleneimino)ethylamine to give N-(3,4-dichlorophenethyl)-N-formyl-1-phenyl-3-[1-(4-benzylpiperidinyl)]-n-propylamine.

1H-NMR(CDCl$_3$, 200 MHz), •1.62(m,4H), 1.90(m,3H), 2.19(m,3H), 2.30(m,2H), 2.56(d,2H), 2.82(m,4H), 3.49(m, 1H), 4.75(m,1H), 6.89(d,1H), 7.08(s,1H), 7.18(t,2H), 7.30 (t,5H), 7.38(t,4H), 8.43(s,1H)

Example 99

N-Formyl-N-methyl-1-phenyl-3-[1-(4-benzylpiperidinyl)]-n-propylamine

The procedure given in Example 93 was followed using N-methyl-1-phenyl-3-[1-(4-benzylpiperidinyl)]-n-propylamine as a reactant, instead of 1-(3,4-dichlorobenzyl)-2-(1-hexamethyleneimino)ethylamine to give N-formyl-N-methyl-1-phenyl-3-[1-(4-benzylpiperidinyl)]-n-propylamine.

1H-NMR(CDCl$_3$, 200 MHz), •1.56(m,2H), 1.68(m,1H), 1.72(m,2H), 2.07(m,2H), 2.23(m,2H), 2.49(m,2H), 2.58(t, 2H), 2.60(s,3H), 3.08(m,2H), 4.19(m,1H), 5.39(m,1H), 7.14 (t,3H), 7.26(m,7H)

Example 100

N-Formyl-1-phenyl-3-[1-(4-benzoylpiperidinyl)]-n-propylamine

The procedure given in Example 93 was followed using 1-phenyl-3-[1-(4-benzoylpiperidinyl)]-n-propylamine as a reactant, instead of 1-(3,4-dichlorobenzyl)-2-(1-hexamethyleneimino)ethylamine to give N-formyl-1-phenyl-3-[1-(4-benzoylpiperidinyl)]-n-propylamine.

1H-NMR(CDCl$_3$, 200 MHz), •1.85(m,4H), 2.03(m,4H), 2.35(m,2H), 2.92(d,1H), 3.12(d,1H), 3.27(m,1H), 5.22(q, 1H), 7.22(m,5H), 7.47(m,3H), 7.92(d,2H), 8.12(d,1H), 8.20 (s,1H)

Example 101

N-{3-[4-(Hydroxy-phenyl-methyl)-piperidin-1-yl]-1-phenyl-propyl}-formamide

The procedure given in Example 93 was followed using 3-[4-(Hydroxy-phenyl-methyl)-piperidin-1-yl]-1-phenyl-propylamine as a reactant, instead of 1-(3,4-dichlorobenzyl)-2-(1-hexamethyleneimino)ethylamine to give N-{3-[4-(Hydroxy-phenyl-methyl)-piperidin-1-yl]-1-phenyl-propyl}-formamide.

1H-NMR(CDCl$_3$, 200 MHz), •1.43(m,2H), 1.63(m,2H), 1.86(m,2H), 2.04(m,2H), 2.32(br,4H), 2.99(m,2H), 3.64(s, 1H), 4.41(d,1H), 5.17(m,1H), 7.35(br,10H), 8.19(s,1H)

Example 102

N-Methyl-1-[4-(tert-butyl)benzyl]-2-(1-hexamethyleneimino)ethylamine

The solution of N-formyl-1-(4-tert-butylbenzyl)-2-(1-hexamethyleneimino)ethylamine (1mmol) in dry THF (50 mL) was added dropwise to a stirred suspension of LiAlH$_4$ (4 equiv) in dry THF (50 mL) with cooling from an ice bath. The solution was stirred at room temperature under an N$_2$ atmosphere overnight. The reaction was quenched by dropwise (with cooling) addition of water (0.3 mL), 15% NaOH (0.3 mL), and finally water (0.3 mL). The precipitated aluminum salts were filtered, and the filter cake was washed with THF. The combined filtrate and washings were evaporated in vacuo to give N-methyl-1-[4-(tert-butyl)benzyl]-2-(1-hexamethyleneimino)ethylamine. The resulting product was dissolved in 6% HCl-MeOH solution and allowed to stir for 2 h. The solvent was removed under reduced pressure and triturated with THF to N-Methyl-1-[4-(tert-butyl)benzyl]-2-(l-hexamethyleneimino)ethylamine: Yield 90%

1H-NMR(CDCl$_3$, 200 MHz), •1.29(s,9H), 1.56(s,8H), 2.03(s,3H), 2.46(m,4H), 2.59(m,6H), 7.15(dd,2H), 7.30(dd, 2H)

Example 103

N,N-Dimethyl-1-[4-(tert-butyl)benzyl]-2-(1-hexamethyleneimino)ethylamine

The procedure given in Example 102 was followed using N-Formyl-N-methyl-1-[4-(tert-butyl)benzyl]-2-(1-hexamethyleneimino)ethylamine as a reactant, instead of N-formyl-1-(4-tert-butylbenzyl)-2-(1-hexamethyleneimino) ethylamine to give N,N-dimethyl-1-[4-(tert-butyl)benzyl]-2-(1-hexamethyleneimino)ethylamine.

1H-NMR(CDCl$_3$, 200 MHz), •1.21(s,9H), 1.48(s,8H), 1.99(s,2H), 2.30(m,7H), 2.58(m,5H), 2.82(m,1H), 7.26(dd, 4H)

Example 104

N-Methyl-1-(3,4-dichlorobenzyl)-2-[1-(4-benzylpiperidinyl)l ethylamine

The procedure given in Example 102 was followed using N-formyl-1-(3,4-dichlorobenzyl)-2-[1-(4-benzylpiperidinyl)]ethylamine and 1M alane as reactants, instead of N-formyl-1-(4-tert-butylbenzyl)-2-(1-hexamethyleneimino) ethylamine and LiAlH$_4$ to give N-methyl-1-(3,4-dichlorobenzyl)-2-[1-(4-benzylpiperidinyl)]ethylamine.

1H-NMR(CDCl$_3$, 200 MHz), •0.89(m,2H), 1.25(m,3H), 1.61(m,4H), 2.17(m,4H), 2.40(s,2H), 2.51(d,2H), 2.78(m, 2H), 2.96(dd,1H), 7.12(m,5H), 7.23(d,2H), 7.35(s,1H)

Example 105

N-Methyl-1-[4-(tert-butyl)benzyl]-2-[1-(4-benzylpiperidinyl)]ethylamine dihydrochloride The procedure given in Example 102 was followed using N-formyl-1-[4-(tert-butyl)benzyl]-2-[1-(4-benzylpiperidinyl)]ethylamine dihydrochloride as a reactant, instead of N-Formyl-1-(4-tert-butylbenzyl)-2-(1-hexamethyleneimino)ethylamine ethylamine to give N-methyl-1-[4-(tert-butyl)benzyl]-2-[1-(4-benzylpiperidinyl)]ethylamine dihydrochloride.

1H-NMR(DMSO-D6, 200 MHz), •1.22(s,9H), 1.79(m, 6H), 2.71(m,4H), 3.06(m,2H), 3.19(m,2H), 3.62m,4H), 4.18 (m,1H), 7.30(m,9H), 9.49(br,1H), 9.69(br,1H), 10.43(br,1H)

Example 106

N-Methyl-1-(2,4-dichlorobenzyl)-2-[1-(4-benzylpiperidinyl)]ethylamine

The procedure given in Example 102 was followed using N-formyl-1-(2,4-dichlorobenzyl)-2-[1-(4-benzylpiperidinyl)]ethylamine and 1M alane as reactants, instead of N-formyl-1-(4-tert-butylbenzyl)-2-(1-hexamethyleneimino) ethylamine and LiAlH$_4$ to give N-methyl-1-(2,4-dichlorobenzyl)-2-[1-(4-benzylpiperidinyl)]ethylamine.

1H-NMR(CDCl$_3$, 200 MHz), •1.25(m,2H), 1.66(m,4H), 2.00(m,1H), 2.17(m,1H), 2.25(m,2H), 2.43(m,6H), 2.78(m, 3H), 2.99(m,1H), 7.11(m,5H), 7.25(d,2H), 7.39(s,1H)

Example 107

N-Methyl-1-phenyl-3-[1-(4-benzylpiperidinyl)]-n-propylamine

The procedure given in Example 102 was followed using N-formyl-1-phenyl-3-[1-(4-benzylpiperidinyl)]-n-propylamine as a reactant, instead of N-formyl-1-(4-tert-butylbenzyl)-2-(1-hexamethyleneimino)ethylamine to give N-methyl-1-phenyl-3-[1-(4-benzylpiperidinyl)]-n-propylamine.

1H-NMR(CDCl$_3$, 200 MHz), •1.30(m,2H), 1.62(m,2H), 1.81(m,2H), 2.01(m,6H), 2.25(d,4H), 2.52(d,2H), 2.89(t, 2H), 7.22(m,10H)

Example 108

N-Methyl-1-phenyl-3-(1-hexamethyleneimino)-n-propylamine

The procedure given in Example 102 was followed using N-formyl-1-phenyl-3-(1-hexamethyleneimino)-n-propylamine as a reactant, instead of N-formyl-1-(4-tert-butylbenzyl)-2-(1-hexamethyleneimino)ethylamine to give N-methyl-1-phenyl-3-(1-hexamethyleneimino)-n-propylamine.

1H-NMR(CDCl₃, 200 MHz), •1.57(br,8H), 1.72(m,1H), 1.89(m,1H), 2.22(s,3H), 2.41(q,2H), 2.57(m,4H), 2.82(br, 1H), 3.52(m,1H), 7.24(m,5H)

Example 109

N,N-Dimethyl-1-phenyl-3-[1-(4-benzylpiperidinyl)]-n-propylamine

The procedure given in Example 102 was followed using N-formyl-N-methyl-1-phenyl-3-[1-(4-benzylpiperidinyl)]-n-propylamine as a reactant, instead of N-formyl-1-(4-tert-butylbenzyl)-2-(1-hexamethyleneimino)ethylamine to give N,N-dimethyl-1-phenyl-3-[1-(4-benzylpiperidinyl)]-n-propylamine.

1H-NMR(CDCl₃, 200 MHz), •1.70(m,4H), 2.18(d,1H), 2.23(s,6H), 2.39(d₁H), 2.58(s,2H), 2.99(m,4H), 3.20(m,2H), 3.48(q,1H), 3.70(t,1H), 7.12(d,2H), 7.21(d,6H), 7.31(t,2H)

Example 110

N-Methyl-1-phenyl-3-[1-(4-(4-fluorobenzoyl)piperidinyl)]-n-propylamine

The procedure given in Example 102 was followed using N-formyl-1-phenyl-3-[1-(4-(4-fluorobenzoyl)piperidinyl)]-n-propylamine and 1M alane as reactants, instead of N-formyl-1-(4-tert-butylbenzyl)-2-(1-hexamethyleneimino) ethylamine and LiAlH₄ to give N-methyl-1-phenyl-3-[1-(4-(4-fluorobenzoyl)piperidinyl)]-n-propylamine.

1H-NMR(CDCl₃, 200 MHz), •1.81(m,4H), 2.01(m,3H), 2.23(s,3H), 2.35(m,1H), 2.60(br,2H), 2.93(d,1H), 3.06(d, 1H), 3.19(m,1H), 3.59(t,1H), 3.63(s,1H), 7.11(t,2H), 7.28 (m,5H), 7.95(q,2H)

What is claimed is:

1. A racemic or enantiomerically enriched phenylalkyldiamine compound represented by the structural formula (I):

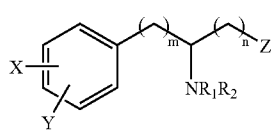

(I)

wherein m is 1, n is 1, X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R₁ and R₂ are hydrogen, and Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II')

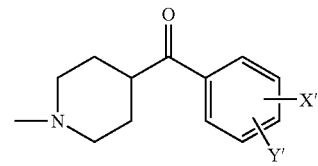

(II)

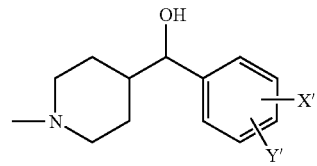

(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

2. A racemic or enantiomerically enriched phenylalkyldiamine compound represented by the structural formula (I):

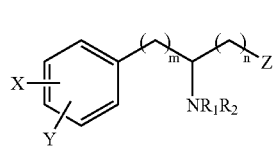

(I)

wherein m is 0, n is 2, X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R₁ and R₂ are hydrogen, and Z is a radical derived from 5 to 7-membered aliphatic cyclic compounds selected from morpholine, 4-benzylpiperidine, N-benzylpiperazine, substituted 4-benzoylpiperidine and their derivatives having the general formula (II) or (II')

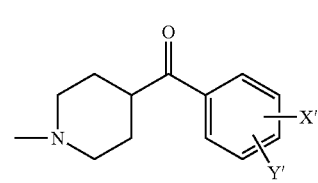

(II)

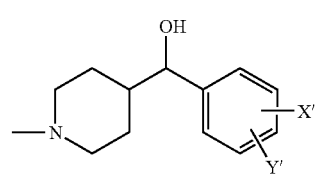

(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

3. A racemic or enantiomerically enriched phenylalkylamino amide compounds represented by the structural formula (XI):

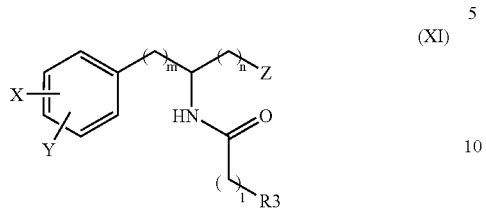

wherein m is 1, n is 1, l is 0–3, X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are selected from the group consisting of hydrogen, phenyl and 3,4-dichlorophenyl; and Z is a radical derived from 5 to 7-membered aliphatic cyclic compounds selected from pyrrolidine, piperidine, hexamethyleneimine, morpholine, 4-benzylpiperidine, N-benzylpiperazine, substituted 4-benzoylpiperidine and their derivatives having the general formula (II) or (II')

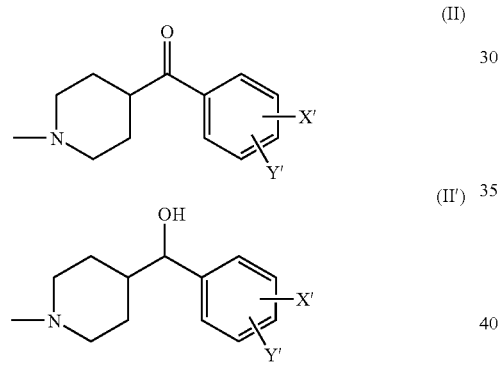

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

4. A racemic or enantiomerically enriched phenylalkylamino amide compounds represented by the structural formula (XI):

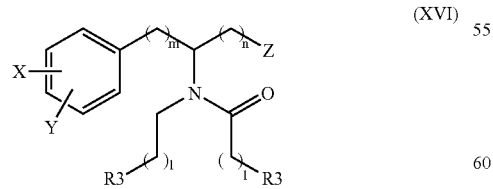

wherein m is 0, n is 2, l is 0–3, X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are selected from the group consisting of hydrogen, phenyl and 3,4-dichlorophenyl; and Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II')

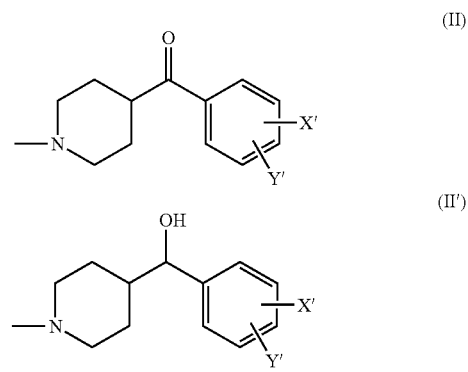

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

5. A racemic or enantiomerically enriched phenylalkylamino amide compounds represented by the structural formula (XVI):

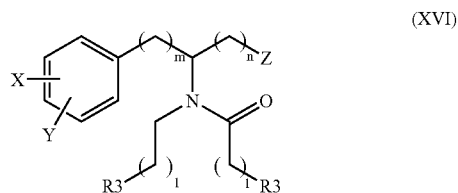

wherein m is 1, n is 1 and l is 0–3; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are independently selected from the group consisting of hydrogen phenyl and 3,4-dichlorophenyl; and Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (III) or (II')

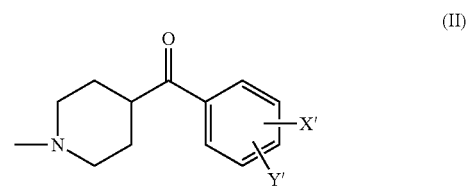

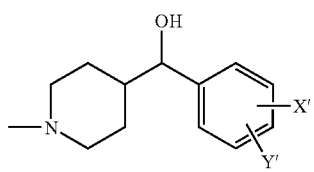

(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

6. A racemic or enantiomerically enriched phenylalkylamino amide compounds represented by the structural formula:

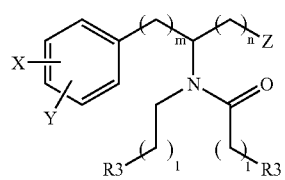

(XVI)

wherein m is 0, n is 2 and l is 0–3; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are independently selected from the group consisting of hydrogen, phenyl and 3,4-dichlorophenyl; and Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II')

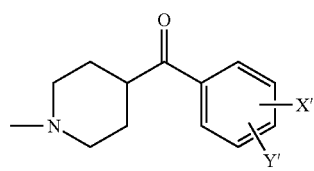

(II)

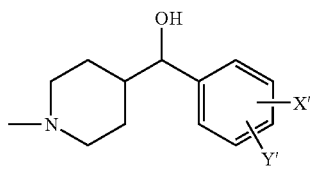

(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

7. A racemic or enantiomerically enriched phenylalkylamino sulfonamide compounds represented by the following structural formula (XIV):

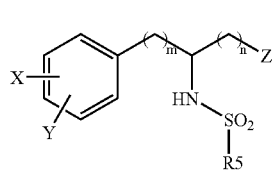

(XIV)

wherein m is 0–2 and n is 1–4; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R5 is selected from the group consisting of methyl, phenyl, 2-nitrophenyl, 4-methylphenyl, 2,4-dinitrophenyl, 3-nitrophenyl, 2,4,6-triisopropylphenyl and 2-thiophenyl; and Z is a radical derived from 5 to 7-membered aliphatic cyclic compounds selected from pyrrolidine, piperidine, hexamethyleneimine, morpholine, 4-benzylpiperidine, N-benzylpiperazine, substituted 4-benzoylpiperidine and their derivatives having the general formula (II) or (II')

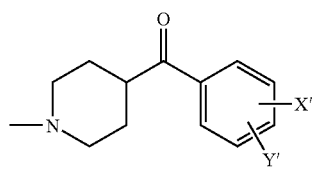

(II)

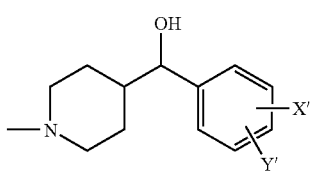

(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; and the pharmaceutically acceptable salts thereof.

8. A racemic or enantiomerically enriched phenylalkylamino sulfonamide compounds represented by the structural formula (XIV), in accordance with claim 7, wherein m is 1, n is 1; R5 is selected from the group consisting of methyl, phenyl, 2-nitrophenyl, 4-methylphenyl, 2,4-dinitrophenyl, 3-nitrophenyl, 2,4,6-triisopropylphenyl and 2-thiophenyl; and Z is a radical derived from 5 to 7-membered aliphatic cyclic compounds selected from pyrrolidine, piperidine, hexamethyleneimine, morpholine, 4-benzylpiperidine, N-benzylpiperazine, substituted 4-benzoylpiperidine and their derivatives having the general formula (II) or (II') and the pharmaceutically acceptable salts thereof.

9. A racemic or enantiomerically enriched phenylalkylamino sulfonamide compounds represented by the structural formula (XIV), in accordance with claim 7, wherein m is 0, n is 2; R5 is selected from the group consisting of methyl, phenyl, 2-nitrophenyl, 4-methylphenyl, 2,4-dinitrophenyl, 3-nitrophenyl, 2,4,6-triisopropylphenyl and 2-thiophenyl; and Z is a radical derived from 5 to 7-membered aliphatic cyclic compounds selected from pyrrolidine, piperidine, hexamethyleneimine, morpholine, 4-benzylpiperidine, N-benzylpiperazine, substituted 4-benzoylpiperidine and their derivatives having the general formula (II) or (II') and the pharmaceutically acceptable salts thereof.

10. A racemic or enantiomerically enriched phenylalkyl-diamine compounds represented by the structural formula (XII):

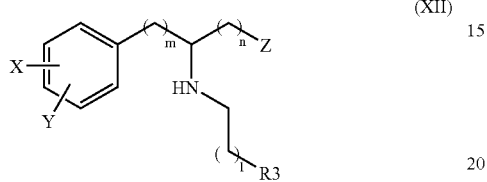

wherein m is 1, n is 1 and l is 0–3; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are selected from the group consisting of hydrogen, phenyl and 3,4-dichlorophenyl; and Z is a radical derived from 5 to 7-membered aliphatic cyclic compounds selected from hexamethyleneimine, 4-benzylpiperidine, N-benzylpiperidine, substituted 4-benzoylpiperidine and their derivatives having the general formula (II) or (II')

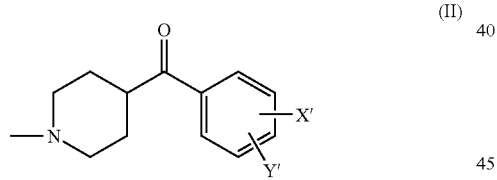

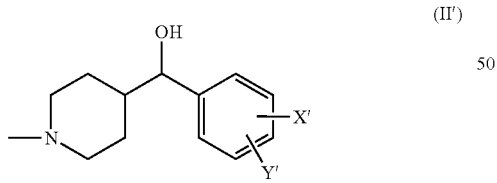

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; and the pharmaceutically acceptable salts thereof.

11. A racemic or enantiomerically enriched phenylalkyl-diamine compounds represented by the structural formula (XII):

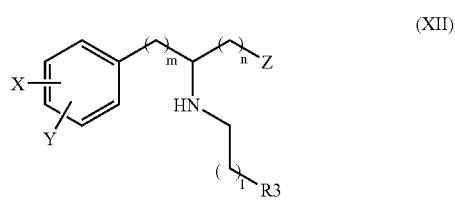

wherein m is 0, n is 2 and l is 0–3; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; R3 are selected from the group consisting of hydrogen, phenyl and 3,4-dichlorophenyl; and Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (III')

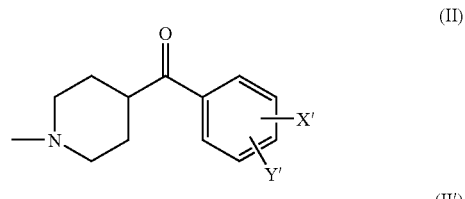

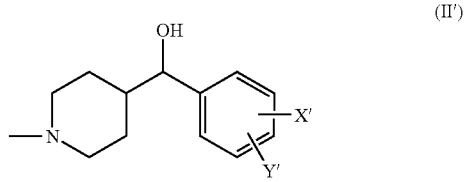

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy and trifluoromethyl; and the pharmaceutically acceptable salts thereof.

12. A racemic or enantiomerically enriched phenylalkyl-diamine compounds represented by the following structural formula (XVII):

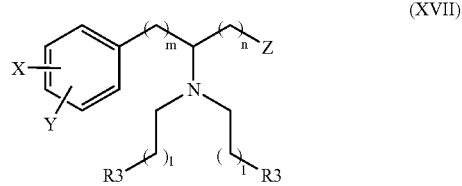

wherein m is 0–2, n is 1–4 and l is 0–3; X and Y are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; R3 are independently selected from the group consisting of hydrogen, phenyl and 3,4-dichlorophenyl; Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II')

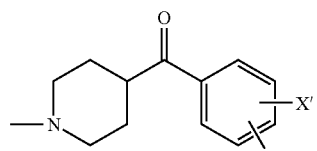
(II)

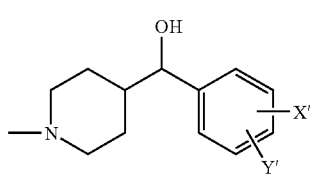
(II')

wherein X' and Y' are independently selected from the group consisting of hydrogen, lower alkyl of 1 to 8 carbon atoms, halogen selected from F, Cl, Br and I, alkoxy containing 1 to 3 carbon atoms, nitro, hydroxy, and trifluoromethyl; and the pharmaceutically acceptable salts thereof.

13. A racemic or enantiomerically enriched phenylalkyldiamine compounds represented by the structural formula (XVII), in accordance with claim 12, wherein m is 1, n is 1 and l is 0–3; R3 are independently selected from the group consisting of hydrogen, phenyl and 3,4-dichlorophenyl; Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II') and the pharmaceutically acceptable salts thereof.

14. A racemic or enantiomerically enriched phenylalkyldiamine compounds represented by the structural formula (XVII), in accordance with claim 12, wherein m is 0, n is 2 and l is 0–3; R3 are independently selected from the group consisting of hydrogen, phenyl and 3,4-dichlorophenyl; Z is a radical derived from 5 to 7-membered aliphatic cyclic compounds selected from hexamethyleneimine, 4-benzylpiperidine, N-benzylpiperazine, substituted 4-benzoylpiperidine and their derivatives having the general formula (II) or (II') and the pharmaceutically acceptable salts thereof.

15. A phenylalkyldiamine and amide compound selected from the group consisting of:
d-1-benzyl-2-(1-hexamethyleneimino)ethylamine dihydrochloride;
l-1-benzyl-2-(N-succinimidyl)ethylamine hydrochloride;
1-(3-chlorobenzyl)-2-(1-hexamethyleneimino)ethylamine dihydrochloride;
1-[4-(tert-butyl)benzyl]-2-(1-hexamethyleneimino)ethylamine dihydrochloride;
1-[4-(trifluoromethyl)benzyl]-2-(1-hexamethyleneimino)ethylamine dihydrochloride;
1-(4-chlorobenzyl)-2-(1-hexamethyleneimino)ethylamine dihydrochloride;
1-(3,4-dichlorobenzyl)-2-(1-hexamethyleneimino)ethylamine dihydrochloride;
1-[3-(trifluoromethyl)benzyl]-2-(1-hexamethyleneimino)ethylamine dihydrochloride;
1-(2,6-dichlorobenzyl)-2-(1-hexamethyleneimino)ethylamine dihydrochloride;
1-(2-methylbenzyl)-2-(1-hexamethyleneimino)ethylamine dihydrochloride;
1-(2,4-dichlorobenzyl)-2-(1-hexamethyleneimino)ethylamine dihydrochloride;
1-(phenethyl)-2-(1-hexamethyleneimino)ethylamine dihydrochloride;
1-(3,4-dichlorobenzyl)-2-[1-(4-benzylpiperidinyl)]ethylamine dihydrochloride;
1-[4-(tert-butyl)benzyl]-2-[1-(4-benzylpiperidinyl)]ethylamine dihydrochloride;
1-(2,4-dichlorobenzyl)-2-[1-(4-benzylpiperidinyl)]ethylamine dihydrochloride;
1-(4-chlorobenzyl)-2-[1-(4-benzoylpiperidinyl)]ethylamine;
1-[4-(tert-butyl)benzyl]-3-[1-(4-benzoylpiperidinyl)]propylamine;
1-[4-(tert-butyl)benzyl]-3-[1-(4-(phenylacetyl)]piperidinyl)]propylamine;
1-[4-(tert-butyl)benzyl]-3-[1-(4-benzylpiperidinyl)]propylamine;
d-1-benzyl-2-[1-(4-benzoylpiperidinyl)]ethylamine;
1-benzyl-2-[1-(4-benzoylpiperidinyl)]ethylamine;
l-1-benzyl-2-[1-(4-benzoylpiperidinyl)]ethylamine;
l-1-benzyl-2-[1-(4-(phenylacetyl)piperidinyl)]ethylamine;
l-1-benzyl-2-[1-(4-(4-chlorobenzoyl)piperidinyl)]ethylamine;
l-1-benzyl-2-[1-(4-(4-fluorobenzoyl)piperidinyl)]ethylamine;
l-1-benzyl-2-[1-(4-(3,4-dichlorobenzoyl)piperidinyl)]ethylamine;
1-(3,4-dichlorobenzyl)-2-[1-(4-benzoylpiperidinyl)]ethylamine;
1-(4-chlorobenzyl)-2-[1-(4-(3,4-dichlorobenzoyl)piperidinyl)]ethylamine;
1-(3,4-dichlorobenzyl)-2-[1-(4-(3,4-dichlorobenzoyl)piperidinyl)]ethylamine;
l-1-benzyl-2-[1-(4-(4-methoxybenzoyl)piperidinyl)]ethylamine;
1-(4-chlorobenzyl)-2-[1-(4-(4-methoxybenzoyl)piperidinyl)]ethylamine;
l-1-benzyl-2-[1-(4-(4-tert-butylbenzoyl)piperidinyl)]ethylamine;
1-[4-(tert-butyl)benzyl]-2-[1-(4-benzoylpiperidinyl)]ethylamine;
1-phenyl-3-[1-(4-benzylpiperidinyl)]-n-propylamine dihydrochloride;
1-phenyl-3-[1-(3-methylpiperidinyl)]-n-propylamine;
1-phenyl-3-[1-(4-benzoylpiperidinyl)]-n-propylamine dihydrochloride;
1-phenyl-3-[1-(1,2,3,4-tetrahydroisoquinolinyl)]-n-propylamine;
1-phenyl-3-[1-(4-(4-fluorobenzoyl)piperidinyl)]-n-propylamine;
1-phenyl-3-[1-(4-(phenylacetyl)piperidinyl)]-n-propylamine;
[1-(3-amino-3-phenyl-propyl)-piperidin-4-yl]-phenyl-methanol;
[1-(3-amino-3-phenyl-propyl)-piperidin-4-yl]-(4-fluoro-phenyl)-methanol;
N-benzoyl-1-(3,4-dichlorobenzyl)-2-(1-hexamethyleneimino)ethylamine;

d-N-(2-nitrobenzenesulfonyl)-1-benzyl-2-(1-pyrrolidinyl)ethylamine hydrochloride;
N-methyl-N-[2-(3,4-dichlorophenyl)acetyl]-1-[4-(tert-butyl)benzyl]-2-(1-hexamethyleneimino)ethylamine;
N-benzoyl-1-(3,4-dichlorobenzyl)-2-[1-(4-benzylpiperidinyl)]ethylamine;
N-[2-(3,4-dichlorophenyl)acetyl]-1-(3,4-dichlorobenzyl)-2-[1-(4-benzylpiperidinyl)]ethylamine;
N-[2-(3,4-Dichlorophenyl)acetyl]-1-(3,4-dichlorobenzyl)-2-(1-hexamethyleneimino)ethylamine;
N-benzoyl-1-(2,4-dichlorobenzyl)-2-[1-(4-benzylpiperidinyl)]ethylamine;
N-[2-(3,4-dichlorophenyl)acetyl]-1-(2,4-dichlorobenzyl]-2-[1-(4-benzylpiperidinyl)]ethylamine;
N-[2-(3,4-dichlorophenyl)acetyl]-1-phenyl-3-(1-hexamethyleneimino)-n-propylamine;
N-(p-toluenesulfonyl)-1-phenyl-3-(1-hexamethyleneimino)-n-propylamine;
N-benzoyl-1-phenyl-3-(1-hexamethyleneimino)-n-propylamine;
N-[2-(3,4-dichlorophenyl)acetyl]-1-phenyl-3-[1-(4-benzylpiperidinyl)]-n-propylamine;
N-[2-(3,4-dichlorophenyl)acetyl]-1-phenyl-3-[1-(4-(4-fluorobenzoylpiperidinyl))-n-propylamine;
N-(p-toluenesulfonyl)-1-phenyl-3-[1-(4-benzylpiperidinyl)]-n-propylamine;
N-(benzenesulfonyl)-1-phenyl-3-[1-(4-benzylpiperidinyl)]-n-propylamine;
N-(2,4-dinitrobenzenesulfonyl)-1-phenyl-3-[1-(4-benzylpiperidinyl)]-n-propylamine;
N-(methanesulfonyl)-1-phenyl-3-[1-(4-benzylpiperidinyl)]-n-propylamine;
N-(3-nitrobenzenesulfonyl)-1-phenyl-3-[1-(4-benzylpiperidinyl)]-n-propylamine;
N-(2-nitrobenzenesulfonyl)-1-phenyl-3-[1-(4-benzylpiperidinyl)]-n-propylamine;
N-(2,4,6-triisopropylbenzenesulfonyl)-1-phenyl-3-[1-(4-benzylpiperidinyl)]-n-propylamine;
N-benzoyl-1-phenyl-3-[1-(4-benzylpiperidinyl) ]-n-propylamine;
N-(2-thiophenesulfonyl)-1-phenyl-3-[1-(4-benzylpiperidinyl)]-n-propylamine;
N-(2-nitrobenzenesulfonyl)-1-phenyl-3-[1-(4-benzoylpiperidinyl)]-n-propylamine;
N-(2-nitrobenzenesulfonyl)-1-phenyl-3-[1-(4-(4-fluorobenzoyl)piperidinyl)]-n-propylamine;
N-(2-thiophenesulfonyl)-1-phenyl-3-[1-(1,2,3,4-tetrahydroisoquinolinyl)]-n-propylamine;
N-benzoyl-1-phenyl-3-[1-(4-benzoylpiperidinyl)]-n-propylamine;
N-[2-(3,4-Dichlorophenyl)acetyl]-1-phenyl-3-[1-(4-benzoylpiperidinyl)]-n-propylamine;
N-benzenesulfonyl-1-phenyl-3-[1-(4-benzoylpiperidinyl)]-n-propylamine;
N-acetyl-1-phenyl-3-[1-(4-benzylpiperidinyl)]-n-propylamine;
N-benzyl-1-(3,4-dichlorobenzyl)-2-(1-hexamethyleneimino)ethylamine;
N-benzyl-1-[4-(tert-butyl)benzyl]-2-(1-hexamethyleneimino)ethylamine;
N-benzyl-1-(3,4-dichlorobenzyl)-2-[1-(4-benzylpiperidinyl)]ethylamine;
N-(3,4-dichlorophenethyl-1-(3,4-dichlorobenzyl)-2-(1-hexamethyleneimino)ethylamine;
N-(3,4-dichlorophenethyl)-1-phenyl-3-(1-hexamethyleneimino)-n-propylamine;
N-(3,4-dichlorophenethyl)-1-phenyl-3-[1-(4-benzylpiperidinyl)]-n-propylamine;
N-formyl-1-(3,4-dichlorobenzyl)-2-(1-hexamethyleneimino)ethylamine;
N-formyl-1-(3,4-dichlorobenzyl)-2-[1-(4-benzylpiperidinyl)]ethylamine;
N-formyl-1-[4-(tert-butyl)benzyl]-2-[1-(4-benzylpiperidinyl)]ethylamine;
N-formyl-1-(2,4-dichlorobenzyl)-2-[1-(4-benzylpiperidinyl)]ethylamine;
N-formyl-1-phenyl-3-[1-(4-benzylpiperidinyl)]-n-propylamine;
N-(3,4-dichlorophenethyl)-N-formyl-1-phenyl-3-[1-(4-benzylpiperidinyl)]-n-propylamine;
N-formyl-N-methyl-1-phenyl-3-[1-(4-benzylpiperidinyl)]-n-propylamine;
N-formyl-1-phenyl-3-[1-(4-benzoylpiperidinyl)]-n-propylamine;
N-{3-[4-(hydroxy-phenyl-methyl)-piperidin-1-yl]-1-phenyl-propyl}-formamide;
N-methyl-1-[4-(tert-butyl)benzyl]-2-(1-hexamethyleneimino)ethylamine;
N,N-dimethyl-1-[4-(tert-butyl)benzyl]-2-(1-hexamethyleneimino)ethylamine;
N-methyl-1-(3,4-dichlorobenzyl)-2-[1-(4-benzylpiperidinyl)]ethylamine;
N-methyl-1-[4-(tert-butyl)benzyl]-2-[1-(4-benzylpiperidinyl)]ethylamine dihydrochloride;
N-methyl-1-(2,4-dichlorobenzyl)-2-[1-(4-benzylpiperidinyl)]ethylamine;
N-methyl-1-phenyl-3-[1-(4-benzylpiperidinyl)]-n-propylamine;
N-methyl-1-phenyl-3-(1-hexamethyleneimino)-n-propylamine;
N,N-dimethyl-1-phenyl-3-[1-(4-benzylpiperidinyl)]-n-propylamine; and
N-methyl-1-phenyl-3-[1-(4-(4-fluorobenzoyl)piperidinyl)]-n-propylamine.

* * * * *